(12) United States Patent
Ji et al.

(10) Patent No.: US 8,906,354 B2
(45) Date of Patent: Dec. 9, 2014

(54) LOADED LATEX OPTICAL MOLECULAR IMAGING PROBES CONTAINING LIPOPHILIC LARGE STOKES SHIFT DYES

(75) Inventors: Tao Ji, Hamden, CT (US); Hans F. Schmitthenner, Rush, NY (US); Yonghong Yang, Hamden, CT (US); John W. Harder, Rochester, NY (US); Jeffrey W. Leon, Placentia, CA (US); William J. Harrison, Pittsford, NY (US); Brian J. Kelley, Farmington, NY (US); James R. Bennett, Rochester, NY (US); David A. Stegman, Churchville, NY (US); Ruizheng Wang, Rochester, NY (US)

(73) Assignee: Bruker Biospin Corporation, Billerica, MA (US)

( * ) Notice: Subject to any disclaimer, the term of this patent is extended or adjusted under 35 U.S.C. 154(b) by 651 days.

(21) Appl. No.: 13/043,057

(22) Filed: Mar. 8, 2011

(65) Prior Publication Data
US 2012/0058050 A1 Mar. 8, 2012

Related U.S. Application Data

(63) Continuation of application No. 12/202,681, filed on Sep. 2, 2008, now abandoned, and a continuation of application No. 12/340,993, filed on Dec. 22, 2008, now abandoned, and a continuation of application No. 11/732,424, filed on Apr. 3, 2007, now abandoned, and a continuation of application No. 11/712,531, filed on Feb. 28, 2007, now Pat. No. 8,017,104.

(60) Provisional application No. 61/311,812, filed on Mar. 9, 2010.

(51) Int. Cl.
*A61K 49/00* (2006.01)
*B82Y 15/00* (2011.01)

(52) U.S. Cl.
CPC ......... *A61K 49/0054* (2013.01); *A61K 49/0032* (2013.01); *A61K 49/0093* (2013.01); *B82Y 15/00* (2013.01)
USPC ....................................................... 424/78.17

(58) Field of Classification Search
None
See application file for complete search history.

(56) References Cited

U.S. PATENT DOCUMENTS

| 3,876,581 A | 4/1975 | Neogi |
| 4,199,363 A | 4/1980 | Chen |

(Continued)

FOREIGN PATENT DOCUMENTS

| EP | 1 065 250 | 12/2004 |
| JP | 2004-252189 | 9/2004 |

(Continued)

OTHER PUBLICATIONS

Commonly Assigned US Publication No. 2007/0237821 (Leon), filed Apr. 10, 2006, entitled: Nanogel-Based Contrast Agents for Optical Molecular Imaging.

(Continued)

*Primary Examiner* — Paul Dickinson
(74) *Attorney, Agent, or Firm* — O'Shea Getz P.C.

(57) ABSTRACT

The present invention relates to a loaded particle comprising at least one fluorescent dye, and in particular, a fluorescent dye with a large Stokes shift. The invention further relates to a method for producing an loaded latex particle, loaded with a fluorescent dye having a large stokes shift. In addition, the present invention relates to latex particles loaded with fluorescent dyes that are organic solvent soluble and insoluble in water. In a preferred embodiment, when the dyes are loaded into the water soluble latex particle, an increase is observed in quantum yield of fluorescence as compared to the quantum yield of the dye in aqueous solvent.

44 Claims, 2 Drawing Sheets

Fluorescence image of dilution series from Loading of Nanolatex 1 with Dye 1

2 fold dilution series

(56) References Cited

U.S. PATENT DOCUMENTS

| | | |
|---|---|---|
| 4,368,258 A | 1/1983 | Fujiwhara et al. |
| 4,520,110 A | 5/1985 | Stryer et al. |
| 4,542,104 A | 9/1985 | Stryer et al. |
| 4,647,447 A | 3/1987 | Gries et al. |
| 4,666,862 A | 5/1987 | Chan |
| 4,677,050 A | 6/1987 | Yokoyama et al. |
| 4,707,454 A | 11/1987 | Hendrix |
| 4,891,324 A | 1/1990 | Pease et al. |
| 4,981,977 A | 1/1991 | Southwick et al. |
| 4,997,772 A | 3/1991 | Sutton et al. |
| 5,078,985 A | 1/1992 | Rhodes |
| 5,286,486 A | 2/1994 | Payne et al. |
| 5,326,692 A | 7/1994 | Bringley et al. |
| 5,364,613 A | 11/1994 | Sieving et al. |
| 5,367,080 A | 11/1994 | Toner et al. |
| 5,453,505 A | 9/1995 | Lee et al. |
| 5,464,741 A | 11/1995 | Hendrix |
| 5,498,875 A | 3/1996 | Obremski et al. |
| 5,532,129 A | 7/1996 | Heller |
| 5,565,322 A | 10/1996 | Heller |
| 5,569,587 A | 10/1996 | Waggoner |
| 5,573,909 A | 11/1996 | Singer et al. |
| 5,580,733 A | 12/1996 | Levis et al. |
| 5,594,047 A | 1/1997 | Nielsen et al. |
| 5,627,027 A | 5/1997 | Waggoner |
| 5,646,264 A | 7/1997 | Glazer et al. |
| 5,763,189 A | 6/1998 | Buechler et al. |
| 5,767,267 A | 6/1998 | Glazer et al. |
| 5,808,044 A | 9/1998 | Bruch et al. |
| 5,809,185 A | 9/1998 | Mitchell |
| 5,849,489 A | 12/1998 | Heller |
| 5,877,310 A | 3/1999 | Reddington et al. |
| 5,990,202 A | 11/1999 | Nguyen et al. |
| 6,008,373 A | 12/1999 | Waggoner et al. |
| 6,043,025 A | 3/2000 | Minden et al. |
| 6,043,690 A | 3/2000 | Krymski et al. |
| 6,090,552 A | 7/2000 | Nazarenko et al. |
| 6,127,134 A | 10/2000 | Minden et al. |
| 6,130,094 A | 10/2000 | Waggoner et al. |
| 6,133,445 A | 10/2000 | Waggoner et al. |
| 6,162,603 A | 12/2000 | Heller |
| 6,168,892 B1 | 1/2001 | Ohara et al. |
| 6,203,973 B1 | 3/2001 | Chen et al. |
| 6,204,068 B1 | 3/2001 | Soini et al. |
| 6,232,075 B1 | 5/2001 | Williams |
| 6,238,931 B1 | 5/2001 | Buechler et al. |
| 6,255,083 B1 | 7/2001 | Williams |
| 6,306,607 B2 | 10/2001 | Williams |
| 6,327,074 B1 | 12/2001 | Bass et al. |
| 6,366,793 B1 | 4/2002 | Bell et al. |
| 6,416,953 B1 | 7/2002 | Heller |
| 6,667,830 B1 | 12/2003 | Iketaki et al. |
| 6,706,460 B1 | 3/2004 | Williams et al. |
| 6,762,048 B2 | 7/2004 | Williams |
| 6,844,154 B2 | 1/2005 | Landers |
| 6,887,662 B1 | 5/2005 | Alajem et al. |
| 6,890,703 B2 | 5/2005 | Hawker et al. |
| 6,911,310 B2 | 6/2005 | Heller |
| 6,951,761 B2 | 10/2005 | Star et al. |
| 6,964,844 B1 | 11/2005 | Buechler et al. |
| 6,969,615 B2 | 11/2005 | Knezevic et al. |
| 6,982,146 B1 | 1/2006 | Schneider et al. |
| 6,995,206 B2 | 2/2006 | Zhou et al. |
| 7,008,768 B1 | 3/2006 | Fornace, Jr. et al. |
| 7,033,524 B2 | 4/2006 | Kumacheva |
| 7,045,319 B2 | 5/2006 | Hanna |
| 7,081,336 B2 | 7/2006 | Bao et al. |
| 7,144,852 B2 | 12/2006 | Ferguson et al. |
| 2002/0113854 A1 | 8/2002 | Erdtmann et al. |
| 2004/0038318 A1 | 2/2004 | Bell |
| 2005/0244976 A1 | 11/2005 | Gee et al. |
| 2006/0029979 A1 | 2/2006 | Bai et al. |
| 2007/0237821 A1 | 10/2007 | Leon et al. |
| 2007/0238656 A1 | 10/2007 | Harder et al. |
| 2008/0181965 A1 | 7/2008 | Leon et al. |
| 2008/0206886 A1 | 8/2008 | Wang et al. |

FOREIGN PATENT DOCUMENTS

| | | |
|---|---|---|
| WO | 93/23492 | 11/1993 |
| WO | 97/40104 | 10/1997 |
| WO | 99/51702 | 10/1999 |
| WO | 02/32464 | 4/2002 |
| WO | 2006/016166 | 2/2006 |
| WO | 2006/019775 | 2/2006 |
| WO | 2007/120579 | 4/2007 |

OTHER PUBLICATIONS

H. Ow et al., "Bright and Stable Core-Shell Fluorescent Nanoparticles", Nano Letters, Nano Letters 2005 vol. 5, pp. 113-117.

Daniel Horak et al., Preparation of Colored Poly(styrene-co-butyl methacrylate) Micrometer Size Beads with Narrow Size Distribution by Dispersion Polumerization in Presence of Dyes, Journal of Polymer Science: Part A: Polymer Chemistry, vol. 33, pp. 2961-2968, 1995.

Mayuko Takasu et al., Preparation of colored latex containing oil-soluable dyes with high dye content by mini-emulsion polymerization, Colloid Polym Sci, vol. 282, pp. 119-126, 2003.

Nynke A.M. Verhaegh et al., Dispersions of Rhodamine-Labeled Silica Spheres: Synthesis, Characterization, and Fluoresence Confocal Scanning Laser Microscopy, Langmuir, 1994, vol. 10, pp. 1427-1438.

A. Imhof et al., Spectroscopy of Fluorescein (FITC) Dyed Colloidal Silica Spheres, J. Phys. Chem. B, vol. 103, pp. 1408-1415.

Ed Harlow, Antibodies, A Laboratory Maual, Chapter 5, Immunizations, Cold Spring Harbor Laboratory, 1988, pp. 91-113.

G. Kohler et al., Derivation of specific antibodyu-producing tissue culture and tumor lines by cell fusion, Eur. J. Immunol. 1976, vol. 6, pp. 511-519.

Greg Winter et al., Man-made antibodies, Nature, vol. 349, Jan. 24, 1991, pp. 293-299.

Albert F. LoBuglio et al., Mouse/human chimeric monoclonal antibody in man: Kinetics and immune response, Proc. Natl. Acad. Sci., vol. 86, pp. 4220-4224, Jun. 1989, Immunology.

Peter A. Lovell et al., Emulsion Polymerization and Emulsion Polymers, Chapter 7, pp. 240-274.

R. Arshady, Suspension, emulsion, and dispersion polymerization: A methodological survey, Colloid Polym Sci, 1992, vol. 270, pp. 717-732.

W.C.W. Chan et al., Quantum Dot Bioconjugates for Ultrasensitive Nonisotopic Detection, Science 1998, vol. 281, pp. 2016-2018.

M.K. Moi et al., The Peptide Way to Macocyclic Bifuntional Chelating Agents: Synthesis of 2-(p-Nitrobenzyl)-1,4,7,10-Tetraazacyclododecane-N,N',N",N"'-Tetraacetic Acid and Study of Its Yttrim (III) Complex, JACS 1998, vol. 110, pp. 6266-6267.

W. Zhao et al., Conformationally Restricted Aza-Bodipy: A Highly Fluorescent, Stable, Near-Infrared-Absorbing Dye, Agnew. Chem. Int. Ed. 2005, 44, 1677.

K. Lou et al., Journal of East China University of Science and Technology, 28, (2), pp. 212-215, 2002.

D.L. Ladd et al., Reagents for the preparation of chromophorically labeled polyethylene glycol-protein conjugates, Analytical Biochemistry, 1993, vol. 210, pp. 258-261.

PCT International Search Report, International Application No. PCT/US09/02801, dated Mar. 30, 2010.

Muirhead et al., Biotechnology, vol. 3, (Apr. 1985), pp. 337-356.

Ozmen et al., Tetrahedron Letters 41, 2000 , pp. 9185-9188.

Mujumdar et al.Bioconjugate Chem., vol. 4, (1993),pp. 105-111.

Mishra, et al., Chem Rev., 2000 , 100, pp. 1973-2011.

Oi et al., J. Cell Bio., vol. 93, Jun. 1982, pp.. 981-986.

(56) References Cited

OTHER PUBLICATIONS

Stryer et al., Energy Transfer: A Spectroscopic Ruler, Proc. Nat'l Acad. Sci., USA, 58, 1967, pp. 719-726.

Haughland et al., Dependence of the Kinetics of Singlet-Singlet Energy Transfer on Spectral Overlap, PNAS 1969;63, pp. 23-30.

D.M. Sturmer, Heterocyclic Compounds Specia Topics in heterocyclic chemistry, John Wiley & Sons, New York & London, 1977, pp. 485-515.

Gorelenko et al., Photonics of Bichromophores Based on Laser Dyes in Solutions and Polymers, Exp. Technik der Physik, vol. 37, 1989, pp. 343-346.

Saito et al., Appl. Phys. Lett., vol. 56, 1990, pp. 811-813.

F.M. Hamer, Heterocyclic Compounds—Cyanine Dyes and Related Compounds,(Chapter VIII—Symmetrical and Unsymmetrical Heptamethincyanines, Including those with Substituents on the Chain; Polymethincyanines), John Wiley & Sons, New York & London , 1964, pp. 244-269.

PCT International Search Report, International Application No. PCT/US2007/008638, pp. 2, 2007.

Fluorescence image of dilution series from Loading of Nanolatex 1 with Dye 1

Fluorescence image of dilution series from Loading of Nanolatex 1 with Dye 2

LOADED LATEX OPTICAL MOLECULAR IMAGING PROBES CONTAINING LIPOPHILIC LARGE STOKES SHIFT DYES

CROSS REFERENCE TO RELATED APPLICATIONS

This is a 111A application of Provisional Application Ser. No. 61/311,812, filed Mar. 9, 2010.

Priority is claimed to U.S. Application No. 61/311,812, provisionally filed on Mar. 9, 2010, entitled LOADED LATEX OPTICAL MOLECULAR IMAGING PROBES CONTAINING LIPOPHILIC LARGE STOKES SHIFT DYES, by Schmitthenner et al.

This is a continuation of U.S. patent application Ser. No. 12/202,681, published as US 2009/0280064 (Papineni), filed on Sep. 2, 2008 now abandoned entitled "TRANSDERMAL DELIVERY OF OPTICAL, SPECT, MULTIMODAL, DRUG OR BIOLOGICAL CARGO LADEN NANOPARTICLE(S) IN SMALL ANIMALS OR HUMANS", incorporated herein by reference This is a continuation of U.S. patent application Ser. No. 12/340,993, published as US 2009/0180964 (Papineni), filed on Dec. 22, 2008 now abandoned entitled "TRANSMUCOSAL DELIVERY OF OPTICAL, SPECT, MULTIMODAL, DRUG OR BIOLOGICAL CARGO LADEN NANOPARTICLE(S) IN SMALL ANIMALS OR HUMANS", incorporated herein by reference This is a continuation of U.S. patent application Ser. No. 11/732,424, published as US 2008/0181965 (Leon) filed on Apr. 3, 2007 now abandoned entitled "LOADED LATEX OPTICAL MOLECULAR IMAGING PROBES", incorporated herein by reference.

This is a continuation of U.S. patent application Ser. No. 11/712,531, published as US 2008/0206886 (Wang) filed on Feb. 28, 2007 now U.S. Pat. No. 8,017,104 entitled "LARGE STOKE SHIFT DYE USED FOR OPTICAL IMAGING", incorporated herein by reference.

Reference is made to U.S. patent application Ser. No. 11/401,343, published as US 2007/0237821 (Leon) filed on Apr. 10, 2006 entitled "NANOGEL-BASED CONTRAST AGENTS FOR OPTICAL MOLECULAR IMAGING", incorporated herein by reference (now abandoned).

FIELD OF THE INVENTION

The present invention relates to fluorescent particles and fluorescent dyes, and uses thereof.

BACKGROUND OF THE INVENTION

Dyes have been incorporated into silica particles. (Ow, H.; Larson, D. R.; Srivastava, M.; Baird, B. A.; Webb, W. W.; Wiesner, U. "Bright and Stable Core-Shell Fluorescent Nanoparticles" Nano Letters 2005, 5, 113-117/Verhaegh, N. A. M.; Blaaderen, A. v. "Dispersions of Rhodamine-Labeled Silica Spheres: Synthesis, Characterization, and Fluorescence Confocal Scanning Laser Microscopy" Langmuir 1994, 10, 1427-1438./Imhof, A.; Megens, M.; Engelberts, J. J.; Lang, D. T. N. d.; Sprik, R.; Vos, W. L. "Spectroscopy of Fluorescein (FITC) Dyed Colloidal Silica Spheres" J. Phys. Chem. B 1999, 103, 1408-1415.).

Loaded latexes with IR dyes have been employed for imaging and photographic applications (for example, refer to US 2002/0113854 and U.S. Pat. No. 6,706,460). Latexes loaded with non-IR dyes are known for biological and diagnostic applications.

US 2008/0181965 describes incorporation of lipophilic versions of dyes, with examples taken largely from the class of carbocyanine dyes, such as those known in the art as Cy3, Cy5, Cy5.5, and Cy7. These dyes do not exhibit a large Stokes shift.

US 2008/0206886 describes structural modifications to the carbocyanine class of dyes which result in remarkable Stokes shifts. The described structures include polar functionality for water solubility attached to the aromatic groups and a functional group on a side chain (R5) which makes it possible to attach the dyes to various bio-molecules like antibodies and other types of proteins and peptides.

US 2005/0244976 relates to methods of detecting anionic proteins in a sample with fluorescent carbocyanine dye compounds. The reference is of use in a variety of fields including immunology, diagnostics, proteomics, molecular biology and fluorescence based assays. Anionic proteins are detected in a sample with fluorescent carbocyanine dye compounds. The reference also describes methods of simultaneously detecting anionic and non-anionic proteins in a sample with discrete fluorescent signals produced by carbocyanine dye compounds.

U.S. Pat. No. 6,964,844 relates generally to the synthesis of novel dyes and labels and methods for the detection or visualization of analytes and more specifically to fluorescent latex particles which incorporate the novel fluorescent dyes and utilize, in certain aspects, fluorescence energy transfer and intramolecular energy transfer, for the detection of analytes in immunoassays or in nucleic acid assays. These dyes are water soluble hybrid phthalocyanine derivatives useful in competitive and noncompetitive assays immunoassays, nucleic acid and assays are disclosed and claimed having (1) at least one donor subunit with a desired excitation peak; and (2) at least one acceptor subunit with a desired emission peak, wherein said derivative(s) is/are capable of intramolecular energy transfer from said donor subunit to said acceptor subunit. Such derivatives also may contain an electron transfer subunit. Axial ligands may be covalently bound to the metals contained in the water soluble hybrid phthalocyanine derivatives. Ligands, ligand analogues, polypeptides, proteins and nucleic acids can be linked to the axial ligands of the dyes to form dye conjugates useful in immunoassays and nucleic acid assays.

U.S. Pat. No. 4,997,772 relates to a core/shell polymer particle containing a detectable tracer material in the core only. It also relates to an immunoreactive reagent and the use of that reagent in analytical elements and methods. A water-insoluble polymeric particle has an inner core comprising a detectable tracer material distributed in a first polymer for which the tracer material has a high affinity. This first polymer has a glass transition temperature ($Tg_1$) less than about 100 degree C. The particle also has an outer shell comprising a second polymer for which the tracer material has substantially less affinity relative to said first polymer. This second polymer has a glass transition temperature ($Tg_2$) which is greater than or equal to the term [$Tg_1-10°$ C.]. It also contains groups which are either reactive with free amino or sulthydryl groups of an immunoreactive species or which can be activated for reaction with such groups. Such a species can be covalently attached to this particle to form an immunoreactive reagent which is useful in analytical elements and various analytical methods including immunological methods, for example, agglutination assays.

US 2004/0038318 relates to a reagent set and to a method, for carrying out simultaneous analyses of multiple isoenzymes in a test sample, including a bodily fluid. The reference describes measuring creatine kinase isoenzymes in particle, or bead, based multiplexed assay systems.

U.S. Pat. No. 4,891,324 relates to methods for performing an assay for determining an analyte by use of a conjugate of a member of a specific binding pair consisting of ligands and receptors, for example, antigens and antibodies, with a particle. The method has application to heterogeneous immunoassays of biological fluids, for example, serum or urine. The method is carried out using a composition that includes a conjugate of a first specific binding pair member with a particle. A luminescer is reversibly associated with a nonaqueous phase of the particle. Where the first specific binding pair member is not complementary to the analyte, a second specific binding pair member that is capable of binding to the first specific binding pair member is employed. Unbound conjugate is separated from conjugate that is bound to the analyte or to the second specific binding pair member. A reagent for enhancing the detectability of the luminescer is added and the light emission of the luminescer acted on by the reagent is measured.

WO 2006/016166 relates to polymeric materials suitable for medical materials. This reference discloses a polymer containing an alkoxyethyl acrylate monomer, a monomer containing a primary, secondary, tertiary or quaternary amine group and a monomer containing an acid group. The polymer composition forms fibers with the preferred size of 0.5 to 2.0 um, which is still not sufficient to provide nanoparticles less than 100 nm in size which are colloidally stable and can be loaded with non-water soluble fluorescent dye for the purposes of diagnostic imaging.

U.S. Pat. No. 5,326,692 relates to polymeric materials incorporating multiple fluorescent dyes to allow for controlled enhancement of the Stokes shift. In particular, the reference describes microparticles incorporating a series of two or more fluorescent compounds having overlapping excitation and emission spectra, resulting in fluorescent microparticles with a desired effective Stokes shift. The novel fluorescent microparticles are useful in applications such as the detection and analysis of biomolecules, such as DNA and RNA, that require a very high sensitivity and in flow cytometric and microscopy analytical techniques. The reference relates to microparticles incorporating a series of two or more fluorescent dyes having overlapping excitation and emission spectra allowing efficient energy transfer from the excitation wavelength of the first dye in the series, transfer through the dyes in the series and re-emitted as an optical signal at the emission wavelength of last dye in the series, resulting in a desired effective Stokes shift which is controlled through selection of appropriate dyes.

IR-emissive nanoparticulate assemblies for physiological imaging suffer from several problems. First, the dyes are often highly aggregated and hence nonemissive. Second, the fluorescence for the dye-nanoparticle assemblies is often inefficient in an aqueous environment. Third, the dyes used in such assemblies are unstable to light and oxygen and bleach readily, which makes handling and administration difficult. Fourth, such assemblies are often colloidally unstable and cytotoxic. The present invention addresses these problems by providing for loaded latexes possessing a combination of properties that make them well suited for specific biological applications. In addition to giving enhanced fluorescence efficiencies, they are highly biocompatible, are resistant to adhesion of serum proteins, and remain well dispersed over as wide range of conditions.

SUMMARY OF THE INVENTION

In an embodiment, the present invention relates to a loaded latex particle comprising a latex material made from a mixture represented by formula $(X)m-(Y)n-(Z)o-(W)p$, wherein Y is at least one monomer with at least two ethylenically unsaturated chemical functionalities; Z is at least one polyethylene glycol macromonomer with an average molecular weight of between 300 and 10,000; W is an ethylenic monomer different from X, Y, or Z; X is at least one water insoluble, alkoxethyl containing monomer; and m, n, o, and p, are the respective weight percentages of each component monomer. The particle may be loaded with a fluorescent dye, and in particular, a fluorescent dye with a large Stokes shift.

DETAILED DESCRIPTION OF THE INVENTION

Figure 1:
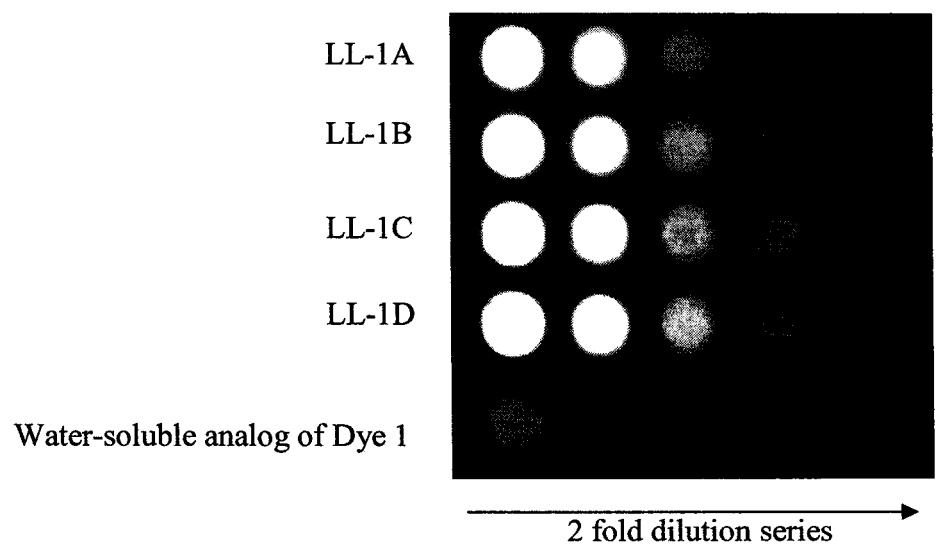
FIG. 1 shows a fluorescence image of dilution series from loading of Nanolatex 1 with Dye 1.

The present invention relates to a loaded latex particle comprising a latex material made from a mixture represented by formula $(X)m-(Y)n-(Z)o-(W)p$, wherein Y is at least one monomer with at least two ethylenically unsaturated chemical functionalities; Z is at least one polyethylene glycol ("PEG") macromonomer with an average molecular weight of between 300 and 10,000; W is an ethylenic monomer different from X, Y, or Z; X is at least one water insoluble, alkoxethyl containing monomer; and m, n, o, and p, are the respective weight percentages of each component monomer. The particle may be loaded with a fluorescent dye and in particular, a fluorescent dye with a large Stokes shift.

The hydrophobic dyes of this invention have the property of a large Stokes shift and may be non-covalently loaded into heavily PEGylated nanolatex particle, which when preferably used in IR-active assemblies, show highly efficient fluorescence, low dye aggregation, and high photostability, that is, are less subject to bleaching. These assemblies are also non-cytotoxic and are very colloidally stable, that is, are less prone to aggregation. The inventive particle demonstrates an increase in the quantum yield of fluorescence. The particle, which may be referred to herein as a nanolatex may be a crosslinked polymer, which is less than 100 nm in size and be composed of alkoxyethyl methacrylate or alkoxyethyl acrylate monomers and is heavily PEGylated.

For purposes of the present invention, the following terms are used: "PEGylated" refers to nanolatex compositions which are composed of at least 5 weight percent covalently bound poly(ethylene glycol). "Pegylation" typically refers to the reaction by which a PEG-protein/peptide conjugate is obtained starting from the activated PEG and the corresponding protein/peptide. This may also apply to PEG-Therapeutic Agent, PEG-Dye, PEG-bioligand, PEG-(MRI Contrast Agent), PEG-(X-Ray Contrast Agent), PEG-Antibody, PEG-(Enzyme Inhibitor) PEG-(radioactive isotope), PEG-(quantum dot), PEG-oligosaccharide, PEG-polygosaccharide, PEG-hormone, PEG-dextran, PEG-oligonucleotide, PEG-carbohydrate, PEG-neurotransmitter, PEG-hapten, PEG-carotinoid.

"Nanolatex" refers to a hydrophobic polymer particle which has a hydrodynamic diameter of less than 100 nm.

A "water dispersible crosslinked polymer particle" refers to a polymer particle which is a contiguous, crosslinked polymer network through which a through-bond path can be traced between any two atoms (not including counterions) in the particle. The particle is capable of existing in water in such a state of division that that each individual particle network is separated from every other by the aqueous continuous phase.

A "hydrophobic crosslinked polymer" refers to a polymer consisting of at least 45 weight percent of water-insoluble monomers. The polymer is a contiguous network through which a through-bond path can be traced between any two atoms (not including counter ions).

"Biocompatible" means that a composition does not disrupt the normal function of the bio-system into which it is introduced. Typically, a biocompatible composition will be compatible with blood and does not otherwise cause an adverse reaction in the body. For example, to be biocompatible, the material should not be toxic, immunogenic or thrombogenic.

"Colloidally stable" refers to the state in which the particle is capable of existing in aqueous phosphate buffered saline (137 mM NaCl, 2.7 mM KCl, 10 mM Na$_2$HPO$_4$, 2 mM KH$_2$PO$_4$ at pH 7.4.) in such a state of division that that each individual particle is separated from every other by the aqueous continuous phase without the formation of agglomerates (entities comprising multiple individual particles in intimate contact) or without bulk flocculation occurring.

"Loaded" or "embedded" refers to a non-covalent association between the dye and the polymer particle such that when the latex is dispersed in water at a concentration of less than 10%, less than 1% of the total dye in the system can be extracted into the water continuous phase.

The latex of this invention is composed of repetitive crosslinked ethylenically unsaturated monomers. The latex may have a volume-average hydrodynamic diameter of 5 and 100 nm, preferably 8 to 50 nm as determined by quasi-elastic light scattering in phosphate buffered saline (137 mM NaCl, 2.7 mM KCl, 10 mM Na$_2$HPO$_4$, 2 mM KH$_2$PO$_4$ at pH 7.4.).

In an embodiment, the loaded latex particle of the invention comprises a latex material made from a mixture represented by the following Formula I:

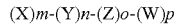  FORMULA I wherein X is at least one water insoluble, alkoxethyl containing monomer; Y is at least one monomer with at least two ethylenically unsaturated chemical functionalities; Z is at least one polyethylene glycol macromonomer with an average molecular weight of between 300 and 10,000; W is an ethylenic monomer different from X, Y, or Z. The weight percent range of each component monomer is represented by m, n, o, and p: m ranges between 40-90 wt %, preferably from 45-60 wt %.; n ranges between 1-10 wt %, preferably 2-6 wt %; o ranges between 20-60 wt %, preferably between 40-50 wt %; and p is up to 10 wt %.

In Formula 1, X is a water-insoluble, alkoxyethyl-containing monomer described below by Formula 2. In Formula 2, R1 is methyl or hydrogen. R2 is an alkyl or aryl group containing up to 10 carbons. Preferably, X is methoxyethyl methacrylate or alkoxyethyl acrylate.

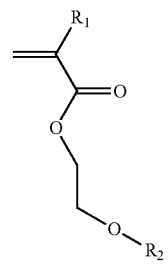

FORMULA 2

In Formula 1, Y is a water-insoluble or water-soluble monomer containing at least two ethylenically unsaturated chemical functionalities. These functionalities may be vinyl groups, acrylates, methacrylates, acrylamides, methacrylamides, allyl groups, vinyl ethers and vinyl esters. Y monomers include, but are not necessarily limited to aromatic divinyl compounds such as divinylbenzene, divinylnaphthalene or derivatives thereof, diethylene carboxylate esters and amides such as ethylene glycol dimethacrylate, diethylene glycol diacrylate, 1,4 butanediol diacrylate, 1,4 butanediol dimethacrylate, 1,3 butylene glycol diacrylate, 1,3 butylene glycol dimethacrylate, cyclohexane dimethanol diacrylate, cyclohexane dimethanol dimethacrylate, diethylene glycol diacrylate, diethylene glycol dimethacrylate, dipropylene glycol diacrylate, dipropylene glycol dimethacrylate, ethylene glycol diacrylate, ethylene glycol dimethacrylate, 1,6 hexanediol diacrylate, 1,6 hexanediol dimethacrylate, neopentyl glycol diacrylate, neopentyl glycol dimethacrylate, tetraethylene glycol diacrylate, tetraethylene glycol dimethacrylate, triethylene glycol diacrylate, triethylene glycol dimethacrylate, tripropylene glycol diacrylate, tripropylene glycol dimethacrylate, pentaerythritol triacrylate, trimethylolpropane triacrylate, trimethylolpropane trimethacrylate, dipentaerythritol pentaacrylate, di-trimethylolpropane tetraacrylate, pentaerythritol tetraacrylate, divinyl esters such as divinyl adipate, and other divinyl compounds such as divinyl sulfide or divinyl sulfone compounds of allyl methacrylate, allyl acrylate, cyclohexanedimethanol divinyl ether diallylphthalate, diallyl maleate, dienes such as butadiene and isoprene and mixtures thereof.

The W monomer can comprise any other inert monomers which are added to modify the properties. W is a non-chemically reactive monomer which can be added in small amounts to impart desired properties to the latex, such as water dispersibility, charge, more facile dye loading, or to make the latex more hydrophobic. For example, W may be a water-soluble monomer such as 2-phosphatoethyl acrylate potassium salt, 3-phosphatopropyl methacrylate ammonium salt, vinylphosphonic acid, and their salts, vinylcarbazole, vinylimidazole, vinylpyrrolidone, vinylpyridines, acrylamide, methacrylamide, maleic acid and salts thereof, sulfopropyl acrylate and methacrylate, acrylic and methacrylic acids and salts thereof, N-vinylpyrrolidone, acrylic and methacrylic esters of alkylphosphonates, styrenics, acrylic and methacrylic monomers containing amine or ammonium functionalities, styrenesulfonic acid and salts thereof, acrylic and methacrylic esters of alkylsulfonates, vinylsulfonic acid and salts thereof, vinylpyridines, hydroxyethyl acrylate, glycerol acrylate and methacrylate esters, (meth)acrylamide, and N-vinylpyrrolidone. W may alternately be a water-insoluble monomer such as methyl methacrylate, ethyl methacrylate, isobutyl methacrylate, 2-ethylhexyl methacrylate, benzyl methacrylate, cyclohexyl methacrylate and glycidyl methacrylate, acrylic/acrylate esters such as methyl acrylate, ethyl acrylate, isobutyl acrylate, 2-ethylhexyl acrylate, benzyl methacrylate, phenoxyethyl acrylate, cyclohexyl acrylate, and glycidyl acrylate, styrenics such as styrene, a-methylstyrene, ethylstyrene, 3- and 4-chloromethylstyrene, halogen-substituted styrenes, and alkyl-substituted styrenes, vinyl halides and vinylidene halides, N-alkylated acrylamides and methacrylamides, vinyl esters such as vinyl acetate and vinyl benzoate, vinyl ether, allyl alcohol and its ethers and esters, and unsaturated ketones and aldehydes such as acrolein and methyl vinyl ketone, isoprene, butadiene and acrylonitrile.

Z is a polyethylene glycol macromonomer with a molecular weight of between 300 and 10,000, preferably between 500 and 5000. In an embodiment, Z is a polyethylene glycol macromonomer represented by a general formula:

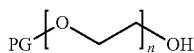

wherein n is greater than 4 and PG is a polymerizable group.

In an embodiment, Z is a linking polymer. Preferably, the linking polymer is a polyethylene glycol backbone chain with specific functional end groups at each end, which allows the polyethylene glycol to act as a linking group between two materials through the two functional end groups.

Preferably, the polyethylene glycol macromonomer contains a radical polymerizable group at one end. This group can be, but is not necessarily limited to a methacrylate, acrylate, acrylamide, methacrylamide, styrenic, allyl, vinyl, maleimide, or maleate ester. Preferably, the polyethylene glycol macromonomer additionally contains a reactive chemical functionality at the other end which can serve as an attachment point for other chemical units, such as quenchers or antibodies. This chemical functionality may be, but is not limited to alcohols, thiols, carboxylic acids, primary or secondary amines, vinylsulfonyls, aldehydes, epoxides, hydrazides, succinimidyl esters, maleimides, a-halo carbonyl moieties (such as iodoacetyls), isocyanates, isothiocyanates, and aziridines. Preferably, these functionalities will be carboxylic acids, primary amines, maleimides, vinylsulfonyls, or secondary amines.

A class of polyethylene glycol macromonomers with a reactive functional group at one end is described by Formula 3.

FORMULA 3

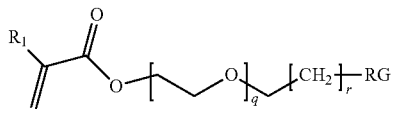

In Formula 3, R1 is hydrogen or methyl, q is 10-200, r is 0-10, and RG is a hydrogen or reactive chemical functionality which can be a alcohol, thiol, carboxylic acid, primary or secondary amine, vinylsulfonyl, aldehyde, epoxy, hydrazide, succinimidyl ester, maleimide, a substituted or unsubstituted acetate, or substituted carbamyl, substituted phosphate, substituted or unsubstituted sulfonate a-halo carbonyl moiety (such as iodoacetyl), isocyanate, isothiocyanate, or aziridine.

In one embodiment, the linking polymer is utilized in two different ways. First, a single linking polymer may be used to attach one functional compound of interest to another, thereby producing a single compound with two different desired functions. Multiple linking polymers may also be attached to a single large particle or bead at one end and a compound of interest on the other, thereby producing a single carrier particle for a large payload of functional compound of interest.

In another embodiment, the linking polymer may be used in both the acylation and alkylation approaches and is compatible with aqueous and organic solvent systems, so that there is more flexibility in reacting with useful groups and the desired products are more stable in an aqueous environment, such as a physiological environment. Preferably, the linking polymer has at least two reactive groups, one of which is an acrylate which is useful for forming nanogels and latexes and reacting with thiols through Michael addition, the other reactive groups is useful for conjugation to contrast agents, dyes, proteins, amino acids, peptides, antibodies, bioligands, therapeutic agents and enzyme inhibitors. The linking polymer may be branched or unbranched. Preferably, for therapeutic use of the end-product preparation, the linking polymer will be pharmaceutically acceptable.

RG in Formula 3 is hydrogen or a reactive chemical functionality. Preferably, the reactive chemical functionality allows the loaded latex to be covalently bonded to a biomolecule and the location of the biomolecule can be determined by fluorescent imaging. The covalent attachment provides a link that is stable to handling, changes in solvent, pH, and ionic strength, and temperature. This stable association between the loaded latex particle and the biomolecule is important to insure that the fluorescent signal that is detected relates to the presence of the biomolecule. If a loaded latex is not covalently attached and associated with the biomolecule through ionic attraction, or Van der Waals forces, then the dye may become detached and the desired biomolecule signal will decrease and false signals may be obtained from the separated loaded latex such that the fluorescence image does not indicate the location of the biomolecule. Alternatively, the reactive chemical functionality (RG) will allow covalent bonding to occur in organic solvents such as N,N-dimethylformamide, dimethylsulfoxide, N-methylpyrrolidone, and non-organic solvents such as water.

In yet another embodiment, the reactive chemical functionality (RG) will allow the use of linkers that are designed to form covalent bonds between the reactive chemical functionality (RG) on the loaded latex and an attachment group on a bio molecule such as an amine, alcohol, carboxylic acid or thiol from amino acids, peptides, protein, cells, RNA, DNA or other linkers which have been added to the biomolecule to allow for greater flexibility in the methods used to attach biomolecules to other materials. Such linkers would include but not be limited to hetero-bifunctional or homo-bifunctional linkers such as bis-sulfosuccinylsuberate, 3-[2-(aminoethyl)dithio]propionic acid, p-azidobenzoylhydrazide, bis-maleimidohexane, N-succinimidyl-S-acetylthioacetate, N-Sulfosuccinimidyl-4-azidophenyl-1-3'-dithiopropionatte, Succinimidyl 4-[p-maleimidophenyl]butyrate, N-Succinimidyl[4-iodoacetyl]aminobenzoate, Sulfosuccinimidyl-[perfluoroazidobenzamido]ethyl-1,3'-dithiopropionate, Succinimidyl 3-[bromoacetamido]propionate, Sulfosuccinimidyl 2-[7-amino-4-methylcoumarin-3-acetamido]ethyl-1,3' dithiopropionate, 3-(2-Pyryldithio)propionyl hydrazide), N-e-Maleimidocaproyloxy]succinimide ester, N-[4-(p-Azidosalicylamido) butyl]-3'-(2'-pyridyldithio)propionamide, Succinimidyl 4-[4N-maleimidomethyl]cyclohexane-1-carboxylate, 4-(4-N-Maleimidophenyl)butyric acid hydrazide hydrochloride, Disuccinimidyl suberate, Lomant's Reagent, Sulfosuccinimidyl[2-6-(biotinamido)-2-(p-azidobenzamido)-hexanoamido]-ethyl-1,3'-dithiopropionate, β-[Tris(hydroxymethyl)phosphino]propionic acid (betaine), (Sulfosuccinimidyl 4-[p-maleimidophenyl]butyrate), Bis-Maleimidoethane, Bis-[b-(4-Azidosalicylamido)ethyl] disulfide, Succinimidyl 4-[N-maleimidomethyl] cyclohexane-1-carboxy-[6-amidocaproate], N-[p-Maleimidophenyl]isocyanate, m-Maleimidobenzoyl-N-hydroxysulfosuccinimide ester, Sulfosuccinimidyl 4-N-maleimidomethyl cyclohexane-1-carboxylate, Bis [sulfosuccinimidyl]suberate, N-[g-Maleimidobutyryloxy] sulfosuccinimide ester, N-succinimidyl 4-pentynoate, and N-succinimidyl 4-azidoylbutanoate.

The reactive chemical functionality may also serve as an attachment point for a metal chelating group used to chelate metals such as radioisotopes (for PET imaging) and Gadolinium (for MRI) imaging. In one embodiment, the metal chelating group is S-2-(4-Isothiocyanatobenzyl)-1,4,7,10 tetraazododecane-tetraacetic acid or 2-(4-Isothiocyanatobenzyl)diethylenetriaminepentaacetic acid. The metal chelating group may be bound to a radioisotope or heavy metal.

The reactive chemical functionality (RG) on the loaded latex can be covalently attached to any drug or biomolecule in such a way to optimize the fluorescent signal and not interfere with the normal function of the biomolecule. Preferably, the carboxylic acid attachment group can be converted to an active ester to enable the covalent bond formation. An N-hydroxysuccinimide ester is a preferred method of activating the carboxylic acid group. The carboxylic acid attachment group can also be activated for covalent bond formation with carbodiimide reagents such as dicylcohexylcarbodiimide. A hydroxyl attachment group can be activated for covalent bond formation by forming a chloroformate such as p-nitrophenyl chloroformate. An amine attachment group can be activated for covalent bond formation by forming using the carbodiimide activating agent to react with carboxylic acid functions of the biomolecule, or forming isocyanates or isothiocyanates or using an amine reactive linking group from the list above. The maleimide linking group can react with thiol groups typically available from cysteine residues in biomolecules or a thiol linking group from the list above, an isocyanate or isothiocyanate can be used directly to react with amine groups of a biomolecule. The trialkoxysilane can be used to react with other trialkoxysilanes or siloxide modified molecules or particles. The alkyne and azidoyl group can be used to form a stable triazole link often catalyzed by copper (I); such that if the dye contains an alkynyl attachment group, then an azidoyl attachment group is placed on the biomolecule or the opposite where an azidoyl group is the attachment group on the dye and an alkynyl group is added to the biomolecule.

A preferred water-soluble linking polymer for use herein is a polyethylene glycol derivative of Formula 4. Polyethylene glycol (PEG) is a hydrophilic, biocompatible and non-toxic polymer of general formula $H(OCH_2CH_2)_nOH$, wherein n>4.

FORMULA 4

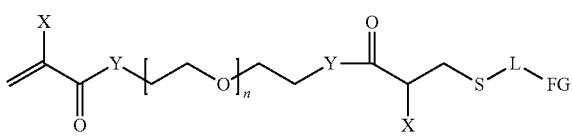

wherein $X=CH_3$ or H, $Y=O$, NR, or S, L is a linking group or spacer, FG is a functional group, n is greater than 4 and less than 1000. Most preferably, $X=CH_3$, $Y=O$, NR, L is alkyl or aryl, and FG is $NH_2$ or COOH, and n is between 6 and 500 or between 10 and 200; more preferably, n=16.

In one embodiment, the linking polymer may be used by attaching to biologically important materials, dyes and contrast agents for detection of disease and the study of metabolic activity, therapeutic agents for the treatment of disease, agents for making thickener agents, pharmaceuticals, and cosmetics. The preferred biologically important materials for attachment of the linking polymer include targeting agents, diagnostic agents, and therapeutic agents, which can be greatly improved in effectiveness when linked.

Targeting agents are compounds with useful groups that will identify and associate with a specific site, such as a disease site, such that the particle or conjugated material will be concentrated in this site for greater effect. Also of particular interest are PEG-antibodies. Antibodies, also known as immunoglobulins (Igs), are proteins that help identify foreign substances to the immune system, such as a bacteria or a virus or any substance bearing an antigen, and are useful for identification and association of specific biological targets. Bioligands are useful groups that will associate with receptor sites expressed in or on cells or with enzymes. Examples of bioligands include growth factors such as biotin and folic acid, specific proteins, and peptide sequences of amino acids or molecules which have strong binding ability to the active sites of enzymes or help the material penetrate or concentrate on or in cells of interest.

Diagnostic agents are materials which enhance the signal of detection when a material is scanned with light, sound, magnetic, electronic and radioactive sources of energy. Examples include dyes such as UV, visible or infrared absorbing dyes especially fluorescent dyes such as indocarbocyanines and fluorescein, MR contrast agents such as gadallinium and iron oxide complexes, and X-ray contrast agents such as a polyiodoaromatic compound. The loaded latex particles can be functionalized with chelating groups such as diethylenteriamepenatacetic acid (DTPA) or 1,4,7,10-tetraazacyclododecane-N,N',N'',N'''-tetra acetic acid (DOTA). These chelating groups can allow the chelating of metals such as gadolinium used in magnetic resonance imaging and X-ray imaging, or technicium used in PET or SPECT imaging. Tetra- and pentaacetic acid chelating groups also allow the loaded latex to be labeled with radioisotopes for radioscintigraphy, single photon emission and positive emission tomography.

The component being labeled can be in a mixture including other materials. The mixture, in which the labeling reaction occurs, can be a liquid mixture, particularly a water mixture. The detection step can occur with the mixture in a liquid or dry condition, such as a microscope slide.

"Labeling" refers to the attachment of the loaded latex or loaded latex conjugate to a material to aid in the identification of the material. Preferably, the material is identified by optical detection methods.

"Biocompatible" means that a composition does not disrupt the normal function of the bio-system into which it is introduced. Typically, a biocompatible composition will be compatible with blood and does not otherwise cause an adverse reaction in the body. For example, to be biocompatible, the material should not be toxic, immunogenic or thrombogenic.

"Biodegradable" means that the material can be degraded either enzymatically or hydrolytically under physiological conditions to smaller molecules that can be eliminated from the body through normal processes. The term "diagnostic agent" includes components that can act as contrast agents and thereby produce a detectable indicating signal in the host or test sample. The detectable indicating signal may be gamma-emitting, radioactive, echogenic, fluoroscopic or physiological signals, or the like.

The term "biomedical agent" as used herein includes biologically active substances which are effective in the treatment of a physiological disorder, pharmaceuticals, enzymes, hormones, steroids, recombinant products and the like. Exemplary therapeutic agents are antibiotics, thrombolytic enzymes such as urokinase or streptokinase, insulin, growth hormone, chemotherapeutics such as adriamycin and antiviral agents such as interferon and acyclovir.

In one embodiment, the loaded latex is associated with a material that is selective for a target material to be labeled and optionally detected. For example, nucleic acid detection generally involves probing a sample thought to contain target nucleic acids using a nucleic acid probe that contains a nucleic acid sequence that specifically recognizes the sequence of the target nucleic acids, such that the nucleic acid probe and the target nucleic acids in combination create a hybridization pair. The nucleic acid probe typically contains from greater than about 4 bases to as many as tens of thousands of bases, although probing entire chromosomes may involve millions of bases. Any of the dye-conjugates described below may be used to label the corresponding target materials.

The component or conjugate to which the loaded latex is attached, also referred to as the labeled component, can be antibodies, proteins, peptides, enzyme substrates, hormones, lymphokines, metabolites, receptors, antigens, haptens, lectins, toxins, carbohydrates, sugars, oligosaccharides, polysaccharides, nucleic acids, deoxy nucleic acids, derivatized nucleic acids, derivatized deoxy nucleic acids, DNA fragments, RNA fragments, derivatized DNA fragments, derivatized RNA fragments, natural drugs, virus particles, bacterial particles, virus components, yeast components, blood cells, blood cell components, biological cells, noncellular blood components, bacteria, bacterial components, natural and synthetic lipid vesicles, synthetic drugs, poisons, environmental pollutants, polymers, polymer particles, glass particles, glass surfaces, plastic particles and plastic surfaces.

A variety of loaded latex-conjugates may be prepared using the loaded latexes of the invention, including conjugates of antigens, steroids, vitamins, drugs, haptens, metabolites, toxins, environmental pollutants, amino acids, peptides, proteins, nucleic acids, nucleic acid polymers, carbohydrates, lipids, and polymers. In another embodiment, the conjugated substance is an amino acid, peptide, protein, polysaccharide, nucleotide, oligonucleotide, nucleic acid, hapten, drug, lipid, phospholipid, lipoprotein, lipopolysaccharide, liposome, lipophilic polymer, polymer, polymeric microparticle, biological cell or virus. In one aspect of the invention, the conjugated substance is labeled with a plurality of loaded latexes of the present invention, which may be the same or different.

The loaded latexes are useful as labels for probes and in immunoassays and also as labels for in-vivo imaging and in-vivo tumor therapy. When so used, these loaded latexes may be linked to one member of a specific binding pair ("labeled binding partner") or an analog of such a member to form a loaded latex-conjugate.

These loaded latexes may be used as agents for in-vivo imaging. When used as imaging agents, these loaded latexes are conjugated to one member of a specific binding pair to give a labeled conjugate/binding complement. The loaded latex-conjugate is introduced into an animal. If the other member of the specific binding pair is present, the loaded latex-conjugate will bind thereto and the signal produced by the dye may be measured and its localization identified.

These loaded latexes may also be used in in-vivo tumor therapy. For example, photodynamic therapy involves using an additional dye component attached to the surface of the nanoparticle as a photosensitizing agent. The loaded latex with photosensitizing agent is further conjugated to a binding partner which may specifically recognize and bind to a component of a tumor cell. The localized triplet emission from the bound dye-loaded latex conjugate after excitation by light, causes chemical reactions and selective damage and/or destruction to the tumor cells.

Target Analyte

In one embodiment, the loaded latex or loaded latex-conjugates are used to probe a sample solution for the presence or absence of a target analyte. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e. drug candidate) is sought.

The target material is optionally a material of biological or synthetic origin that is present as a molecule or as a group of molecules, including, but not limited to, antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatized nucleic acids (including deoxyribo- and ribonucleic acids), DNA and RNA fragments and derivatized fragments (including single and multi-stranded fragments), natural and synthetic drugs, receptors, virus particles, bacterial particles, virus components, biological cells, spores, cellular components (including cellular membranes and organelles), natural and synthetic lipid vesicles, polymer membranes, polymer surfaces and particles, and glass and plastic surfaces and particles. Typically the target material is present as a component or contaminant of a sample taken from a biological or environmental system. Particularly preferred analytes are nucleic acids and proteins.

In one aspect of the invention, the conjugate is a bioreactive substance. The target material is optionally a bioreactive substance also. Bioreactive substances are substances that react with or bind to molecules that are derived from a biological system, whether such molecules are naturally occurring or result from some external disturbance of the system (e.g. disease, poisoning, genetic manipulation). By way of illustration, bioreactive substances include biomolecules (i.e. molecules of biological origin including, without limitation, polymeric biomolecules such as peptides, proteins, polysaccharides, oligonucleotides, avidin, streptavidin, DNA and RNA, as well as non-polymeric biomolecules such as biotin and digoxigenin and other haptens typically having a MW less than 1000), microscopic organisms such as viruses and bacteria, and synthetic haptens (such as hormones, vitamins, or drugs). Typically the target complement or the target material or both are amino acids, peptides (including polypeptides), or proteins (larger MW than polypeptides); or are nucleotides, oligonucleotides (less than 20 bases), or nucleic acids (i.e. polymers larger than oligonucleotides, including RNA and single- and multi-stranded DNA and fragments and derivitized fragments thereof); or are carbohydrates or carbohydrate derivatives, including monosaccharides, polysaccharides, oligosaccharides, glycolipids, and glycoproteins; or are haptens (a chemical compound that is unable to elicit an immunological response unless conjugated to a larger carrier molecule), which haptens are optionally conjugated to other biomolecules; or a microscopic organisms or components of microscopic organisms. For such bioreactive substances, there are a variety of known methods for selecting useful pairs of corresponding conjugates complementary to the target materials.

Where more than one material is targeted simultaneously, multiple conjugates which are target complements (one for each corresponding target material) are optionally included. Target complements are selected to have the desired degree of specificity or selectivity for the intended target materials.

In one embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins. In a preferred embodiment, the target analyte is a nucleic acid. In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected.

In another embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria.

RME

The described composition can further comprise a biological, pharmaceutical or diagnostic component that includes a targeting moiety that recognizes a specific target cell. Recognition and binding of a cell surface receptor through a targeting moiety associated with loaded latexes can be a feature of the described compositions. This feature takes advantage of the understanding that a cell surface binding event is often the initiating step in a cellular cascade leading to a range of events, notably receptor-mediated endocytosis. The term "receptor mediated endocytosis" ("RME") generally describes a mechanism by which, catalyzed by the binding of a ligand to a receptor disposed on the surface of a cell, a receptor-bound ligand is internalized within a cell. Many proteins and other structures enter cells via receptor mediated endocytosis, including insulin, epidermal growth factor, growth hormone, thyroid stimulating hormone, nerve growth factor, calcitonin, glucagon and many others.

Receptor Mediated Endocytosis (hereinafter "RME") affords a convenient mechanism for transporting a dye-conjugate, possibly in combination with other biological, pharmaceutical or diagnostic components, to the interior of a cell.

In RME, the binding of a ligand by a receptor disposed on the surface of a cell can initiate an intracellular signal, which can include an endocytosis response. Thus, a loaded latex with a targeting moiety associated to form a loaded latex-conjugate, can bind on the surface of a cell and subsequently be invaginated and internalized within the cell. A representative, but non-limiting, list of moieties that can be employed as targeting agents useful with the present compositions is selected from the group consisting of proteins, peptides, aptomers, small organic molecules, toxins, diptheria toxin, pseudomonas toxin, cholera toxin, ricin, concanavalin A, Rous sarcoma virus, Semliki forest virus, vesicular stomatitis virus, adenovirus, transferrin, low density lipoprotein, transcobalamin, yolk proteins, epidermal growth factor, growth hormone, thyroid stimulating hormone, nerve growth factor, calcitonin, glucagon, prolactin, luteinizing hormone, thyroid hormone, platelet derived growth factor, interferon, catecholamines, peptidomimetrics, glycolipids, glycoproteins and polysaccharides. Homologs or fragments of the presented moieties can also be employed. These targeting moieties can be associated with loaded latex and be used to direct the loaded latex-conjugate to a target cell, where it can subsequently be internalized. There is no requirement that the entire moiety be used as a targeting moiety. Smaller fragments of these moieties known to interact with a specific receptor or other structure can also be used as a targeting moiety.

An antibody or an antibody fragment represents a class of most universally used targeting moiety that can be utilized to enhance the uptake of loaded latex or loaded latex-conjugate into a cell. Antibodies may be prepared by any of a variety of techniques known to those of ordinary skill in the art. See, e.g., Harlow and Lane, *Antibodies: A Laboratory Manual*, Cold Spring Harbor Laboratory Press, 1988. Antibodies can be produced by cell culture techniques, including the generation of monoclonal antibodies or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). A superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, "Derivation of specific antibody-producing tissue culture and tumor lines by cell fusion." Eur. J. Immunol. 6:511-519, 1976, and improvements thereto.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides may be used in the purification process in, for example, an affinity chromatography step.

A number of "humanized" antibody molecules comprising an antigen-binding site derived from a non-human immunoglobulin have been described Winter et al. (1991) Nature 349:293-299; Lobuglio et al. (1989) Proc. Nat. Acad. Sci. USA 86:4220-4224. These "humanized" molecules are designed to minimize unwanted immunological response toward rodent antihuman antibody molecules that limits the duration and effectiveness of therapeutic applications of those moieties in human recipients.

Vitamins and other essential minerals and nutrients can be utilized as targeting moiety to enhance the uptake of loaded latex or loaded latex-conjugate by a cell. In particular, a vitamin ligand can be selected from the group consisting of folate, folate receptor-binding analogs of folate, and other folate receptor-binding ligands, biotin, biotin receptor-binding analogs of biotin and other biotin receptor-binding ligands, riboflavin, riboflavin receptor-binding analogs of riboflavin and other riboflavin receptor-binding ligands, and thiamin, thiamin receptor-binding analogs of thiamin and other thiamin receptor-binding ligands. Additional nutrients believed to trigger receptor mediated endocytosis, and thus also having application in accordance with the presently disclosed method, are carnitine, inositol, lipoic acid, niacin, pantothenic acid, pyridoxal, and ascorbic acid, and the lipid soluble vitamins A, D, E and K. Furthermore, any of the "immunoliposomes" (liposomes having an antibody linked to the surface of the liposome) described in the prior art are suitable for use with the described loaded latex or loaded latex-conjugates.

Since not all natural cell membranes possess biologically active biotin or folate receptors, use of the described compositions in-vitro on a particular cell line can involve altering or otherwise modifying that cell line first to ensure the presence of biologically active biotin or folate receptors. Thus, the number of biotin or folate receptors on a cell membrane can be increased by growing a cell line on biotin or folate deficient substrates to promote biotin and folate receptor production, or by expression of an inserted foreign gene for the protein or apoprotein corresponding to the biotin or folate receptor.

RME is not the exclusive method by which the loaded latex or loaded latex-conjugates can be translocated into a cell. Other methods of uptake that can be exploited by attaching the appropriate entity to a, loaded latex or loaded latex-conjugate include the advantageous use of membrane pores. Phagocytotic and pinocytotic mechanisms also offer advantageous mechanisms by which a loaded latex or loaded latex-conjugate can be internalized inside a cell.

The recognition moiety can further comprise a sequence that is subject to enzymatic or electrochemical cleavage. The recognition moiety can thus comprise a sequence that is susceptible to cleavage by enzymes present at various locations inside a cell, such as proteases or restriction endonucleases (e.g. DNAse or RNAse).

Biomedical Application

The water dispersible, loaded latex may also be useful in other biomedical applications, including, but not limited to, tomographic imaging of organs, monitoring of organ functions, coronary angiography, fluorescence endoscopy, detection, imaging, determining efficacy of drug delivery, and therapy of tumors, laser assisted guided surgery, photoacoustic methods, and sonofluorescent methods.

The compositions of the invention can be formulated into diagnostic compositions for enteral or parenteral administration. These compositions contain an effective amount of the dye along with conventional pharmaceutical carriers and excipients appropriate for the type of administration contemplated. For example, parenteral formulations advantageously contain a sterile aqueous solution or suspension of dye according to this invention. Parenteral compositions may be injected directly or mixed with a large volume parenteral composition for systemic administration. Such solutions also may contain pharmaceutically acceptable buffers and, optionally, electrolytes such as sodium chloride.

Formulations for enteral administration may vary widely, as is well known in the art. In general, such formulations are liquids which include an effective amount of the dye in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement. Such doses may vary widely, depending upon the particular dye employed, the organs or tissues which are the subject of the imaging procedure, the imaging equipment being used, and the like.

The diagnostic compositions of the invention are used in the conventional manner. The compositions may be administered to a patient, typically a warm-blooded animal, either systemically or locally to the organ or tissue to be imaged, and the patient then subjected to the imaging procedure.

Administration techniques include parenteral administration, intravenous administration and infusion directly into any desired target tissue, including but not limited to a solid tumor or other neoplastic tissue. Purification can be achieved by employing a final purification step, which disposes the loaded latex or loaded latex-conjugate composition in a medium comprising a suitable pharmaceutical composition. Suitable pharmaceutical compositions generally comprise an amount of the desired loaded latex or loaded latex conjugate with active agent in accordance with the dosage information (which is determined on a case-by-case basis). The described particles are admixed with an acceptable pharmaceutical diluent or excipient, such as a sterile aqueous solution, to give an appropriate final concentration. Such formulations can typically include buffers such as phosphate buffered saline (PBS), or additional additives such as pharmaceutical excipients, stabilizing agents such as BSA or HSA, or salts such as sodium chloride.

For parenteral administration it is generally desirable to further render such compositions pharmaceutically acceptable by insuring their sterility, non-immunogenicity and non-pyrogenicity. Such techniques are generally well known in the art. Moreover, for human administration, preparations should meet sterility, pyrogenicity, and general safety and purity standards as required by FDA Office of Biological Standards. When the described loaded latex or loaded latex-conjugate composition is being introduced into cells suspended in a cell culture, it is sufficient to incubate the cells together with the nanoparticle in an appropriate growth media, for example Luria broth (LB) or a suitable cell culture medium. Although other introduction methods are possible, these introduction treatments are preferable and can be performed without regard for the entities present on the surface of a loaded latex carrier.

In one embodiment, the loaded latex-conjugates described above, whether for single or multicolor detection systems, are combined with a sample thought to contain target materials. Typically the sample is incubated with an aqueous suspension of the loaded latex-conjugates. Where a single color detection system is used, the aqueous suspension contains substantially identical, loaded latex-conjugates. Where a multicolor detection system is used, the aqueous suspension contains a number of detectably different loaded latex-conjugates. In each case, the loaded latex-conjugates are specific for a particular target or combination of targets.

Prior to combination with the loaded latex-conjugates, the sample may be prepared in a way that makes the target materials in the sample accessible to the probes. The target materials may require purification or separation prior to labeling or detection. For example, the sample may contain purified nucleic acids, proteins, or carbohydrates, either in mixtures or individual nucleic acid, protein, or carbohydrate species; the sample may contain nucleic acids, proteins, or carbohydrates in lysed cells along with other cellular components; or the sample may contain nucleic acids, proteins, or carbohydrates in substantially whole, permeabilized cells. Preparation of the sample will depend on the way the target materials are contained in the sample. When the sample contains cellular nucleic acids (such as chromosomal or plasmid borne genes within cells, RNA or DNA viruses or mycoplasma infecting cells, or intracellular RNA) or proteins, preparation of the sample involves lysing or permeabilizing the cell, in addition to the denaturation and neutralization already described.

Following the labeling of the sample with the loaded latex-conjugates, unbound loaded latex-conjugates are optionally removed from the sample by conventional methods such as washing.

Detection

For detection of the target materials, the sample is illuminated with means for exciting fluorescence in the loaded latex-conjugates. Typically a source of excitation energy emitting within the range of the excitation peak of the loaded latex-conjugates is used. Fluorescence resulting from the illuminated, loaded latex-conjugates that have formed a complex with the target materials can be used to detect the presence, location, or quantity of target materials.

Fluorescence from the loaded latex-conjugates can be visualized with a variety of imaging techniques, including ordinary light or fluorescence microscopy and laser scanning confocal microscopy and CCD cameras. Three-dimensional imaging resolution techniques in confocal microscopy utilize knowledge of the microscope's point spread function (image of a point source) to place out-of-focus light in its proper perspective. Multiple labeled target materials are optionally resolved spatially, chronologically, by size, or using detectably different spectral characteristics (including excitation and emission maxima, fluorescence intensity, or combinations thereof). Typically, multiple labeled target materials are resolved using different loaded latex conjugates with distinct spectral characteristics for each target material. Alternatively, the loaded latex-conjugates are the same but the samples are labeled and viewed sequentially or spatially separated. If there is no need or desire to resolve multiple targets, as in wide scale screening (e.g. pan-viral or bacterial contamination screening), loaded latex-conjugates containing multiple target complements need not be separately applied to samples.

Therapeutic agents are materials which effect enhance or inhibit cellular function, blood flow, or biodistribution, or bioabsorbtion. Examples would be pharmaceutical drugs for cancer, heart disease, genetic disorders, bacterial and viral infection and many other disorders.

Other useful materials to conjugate would be: PEG-peptide, PEG-protein, PEG-enzyme inhibitor PEG-oligosaccharide, PEG-polygosaccharide, PEG-hormone, PEG-dextran, PEG-oligonucleotide, PEG-carbohydrate, PEG-neurotransmitter, PEG-hapten, PEG-carotinoid.

The PEG could be functionalized with mixtures of these materials to improve effectiveness.

The following is a partial list of preferred linking polymers, but is not intended to be an exhaustive and complete list of all linking polymers according to the present invention:

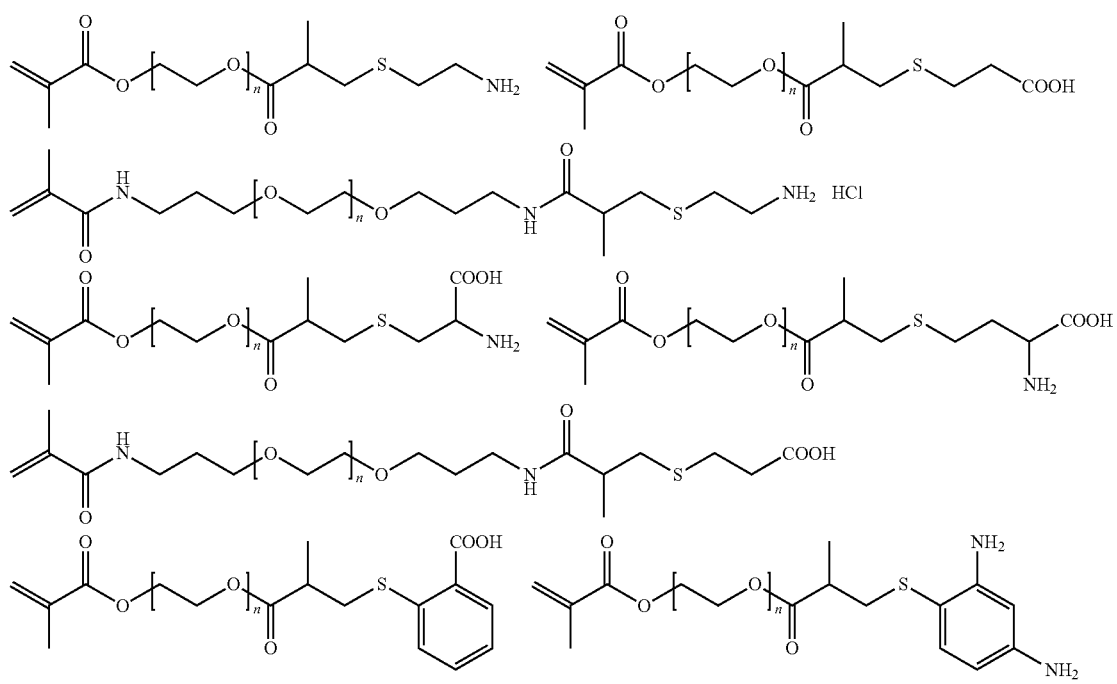

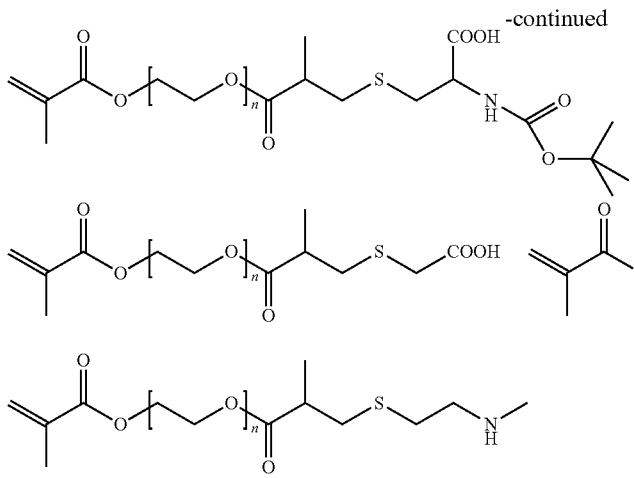

In one embodiment, multiple linking polymers are attached to a nanogel. For example, a first mixture of monomer(s) of interest, the linking polymer, and initiator is prepared in water. The first mixture was added to the second mixture of additional initiator and reacted, after which, additional initiator may be added to produce a nanogel composition. In another preferred embodiment, multiple linking polymers are attached to a nanolatex. A mixture of monomers, linking polymer, initiator, surfactant, and buffer was prepared in water. The mixture is added to an aqueous solution of initiator, surfactant and buffer and reacted to produce a nanolatex particle according to the present invention.

In general, the derivatization may be performed under any suitable condition to react a biologically active substance with an activated water soluble linking polymer molecule. In general, the optimal reaction conditions for the acylation reactions will be determined case-by-case based on known parameters and the desired result. For example, the larger the ratio of PEG: protein, the greater the percentage of polypegylated product. One may choose to prepare a mixture of linking polymer/polypeptide conjugate molecules by acylation and/or alkylation methods, and the advantage provided herein is that one may select the proportion of monopolymer/polypeptide conjugate to include in the mixture.

The latexes useful in this invention may be prepared by any method known in the art for preparing particles of 5-100 nm in mean diameter. Especially useful methods include emulsion and miniemulsion polymerization. Such techniques are reviewed in "Suspension, Emulsion, and Dispersion Polymerization: a Methodological Survey" Colloid. Polym. Sci. vol. 270, p. 717-732, 1992 and in Lovell, P. A.; El-Aaser, M. S. "Emulsion Polymerization and Emulsion Polymers", Wiley: Chichester, 1997. An alternate method involves intramolecularly crosslinking individual polymer chains to form very small particles. This method is described in U.S. Pat. No. 6,890,703.

Dyes useful for this invention include fluorescent, hydrophobic dyes which fluoresce at 400-1000 nm. Classes of dyes include, but are not necessarily limited to oxonol, pyrylium, Squaric, croconic, rodizonic, polyazaindacenes or coumarins, scintillation dyes (usually oxazoles and oxadiazoles), aryl- and heteroaryl-substituted polyolefins ($C_2$-$C_8$ olefin portion), merocyanines, carbocyanines, phthalocyanines, oxazines, carbostyryl, porphyrin dyes, dipyrrometheneboron difluoride dyes aza-dipyrrometheneboron difluoride dyes and oxazine dyes. Commercially available fluorescent dyes are listed in Table 1 and generic structures are shown in Table 2. Preferred dyes include carbocyanine, phthalocyanine, or aza-dipyrrometheneboron difluoride.

TABLE 1

Commercially Available Fluorescent Dyes.

5-Amino-9-diethyliminobenzo(a)phenoxazonium Perchlorate
7-Amino-4-methylcarbostyryl
7-Amino-4-methylcoumarin
7-Amino-4-trifluoromethylcoumarin
3-(2'-Benzimidazolyl)-7-N,N-diethylaminocoumarin
3-(2'-Benzothiazolyl)-7-diethylaminocoumarin
2-(4-Biphenylyl)-5-(4-t-butylphenyl)-1,3,4-oxadiazole
2-(4-Biphenylyl)-5-phenyl-1,3,4-oxadiazole
2-(4-Biphenyl)-6-phenylbenzoxazole-1,3
2,5-Bis-(4-biphenylyl)-1,3,4-oxadiazole
2,5-Bis-(4-biphenylyl)-oxazole
4,4'''-Bis-(2-butyloctyloxy)-p-quaterphenyl
p-Bis(o-methylstyryl)-benzene
5,9-Diaminobenzo(a)phenoxazonium Perchlorate
4-Dicyanomethylene-2-methyl-6-(p-dimethylaminostyryl)-4H-pyran
1,1'-Diethyl-2,2'-carbocyanine Iodide
1,1'-Diethyl-4,4'-carbocyanine Iodide
3,3'-Diethyl-4,4',5,5'-dibenzothiatricarbocyanine Iodide
1,1'-Diethyl-4,4'-dicarbocyanine Iodide
1,1'-Diethyl-2,2'-dicarbocyanine Iodide
3,3'-Diethyl-9,11-neopentylenethiatricarbocyanine Iodide
1,3'-Diethyl-4,2'-quinolyloxacarbocyanine Iodide
1,3'-Diethyl-4,2'-quinolylthiacarbocyanine Iodide
3-Diethylamino-7-diethyliminophenoxazonium Perchlorate
7-Diethylamino-4-methylcoumarin
7-Diethylamino-4-trifluoromethylcoumarin
7-Diethylaminocoumarin
3,3'-Diethyloxadicarbocyanine Iodide
3,3'-Diethylthiacarbocyanine Iodide
3,3'-Diethylthiadicarbocyanine Iodide
3,3'-Diethylthiatricarbocyanine Iodide
4,6-Dimethyl-7-ethylaminocoumarin
2,2'''-Dimethyl-p-quaterphenyl
2,2'''-Dimethyl-p-terphenyl
7-Dimethylamino-1-methyl-4-methoxy-8-azaquinolone-2
7-Dimethylamino-4-methylquinolone-2
7-Dimethylamino-4-trifluoromethylcoumarin
2-(4-(4-Dimethylaminophenyl)-1,3-butadienyl)-3-ethylbenzothiazolium Perchlorate
2-(6-(p-Dimethylaminophenyl)-2,4-neopentylene-1,3,5-hexatrienyl)-3-methylbenzothiazolium Perchlorate
2-(4-(p-Dimethylaminophenyl)-1,3-butadienyl)-1,3,3-trimethyl-3H-indolium Perchlorate
3,3'-Dimethyloxatricarbocyanine Iodide
2,5-Diphenylfuran
2,5-Diphenyloxazole
4,4'-Diphenylstilbene

TABLE 1-continued

Commercially Available Fluorescent Dyes.

1-Ethyl-4-(4-(p-Dimethylaminophenyl)-1,3-butadienyl)-pyridinium Perchlorate
1-Ethyl-2-(4-(p-Dimethylaminophenyl)-1,3-butadienyl)-pyridinium Perchlorate
1-Ethyl-4-(4-(p-Dimethylaminophenyl)-1,3-butadienyl)-quinolium Perchlorate
3-Ethylamino-7-ethylimino-2,8-dimethylphenoxazin-5-ium Perchlorate
9-Ethylamino-5-ethylamino-10-methyl-5H-benzo(a)phenoxazonium Perchlorate
7-Ethylamino-6-methyl-4-trifluoromethylcoumarin
7-Ethylamino-4-trifluoromethylcoumarin
1,1',3,3,3',3'-Hexamethyl-4,4',5,5'-dibenzo-2,2'-indotricarboccyanine Iodide
1,1',3,3,3',3'-Hexamethylindodicarbocyanine Iodide
1,1',3,3,3',3'-Hexamethylindotricarbocyanine Iodide
2-Methyl-5-t-butyl-p-quaterphenyl
3-(2'-N-Methylbenzimidazolyl)-7-N,N-diethylaminocoumarin
2-(1-Naphthyl)-5-phenyloxazole
2,2'-p-Phenylen-bis(5-phenyloxazole)
3,5,3"",5""'-Tetra-t-butyl-p-sexiphenyl
3,5,3"",5""'-Tetra-t-butyl-p-quinquephenyl
2,3,5,6-1H,4H-Tetrahydro-9-acetylquinolizino-<9,9a,1-gh> coumarin
2,3,5,6-1H,4H-Tetrahydro-9-carboethoxyquinolizino-<9,9a,1-gh> coumarin
2,3,5,6-1H,4H-Tetrahydro-8-methylquinolizino-<9,9a,1-> coumarin
2,3,5,6-1H,4H-Tetrahydro-9-(3-pyridyl)-quinolizino-<9,9a,1-gh> coumarin
2,3,5,6-1H,4H-Tetrahydro-8-trifluoromethylquinolizino-<9,9a,1-gh> coumarin
2,3,5,6-1H,4H-Tetrahydroquinolizino-<9,9a,1-gh> coumarin
3,3',2'',3'''-Tetramethyl-p-quaterphenyl
2,5,2'''',5''''-Tetramethyl-p-quinquephenyl
P-terphenyl
P-quaterphenyl
Nile Red
Rhodamine 700
Oxazine 750
Rhodamine 800
IR 125
IR 144
IR 140
IR 132
IR 26
IR 5
Diphenylhexatriene
Diphenylbutadiene
Tetraphenylbutadiene
Naphthalene
Anthracene
Pyrene
Chrysene
Rubrene
Coronene
Phenanthrene
Fluorene
Aluminum phthalocyanine
Platinum octaethylporphyrin

TABLE 2

Illustrative Examples of Fluorescent Dyes

TABLE 2-continued
Illustrative Examples of Fluorescent Dyes
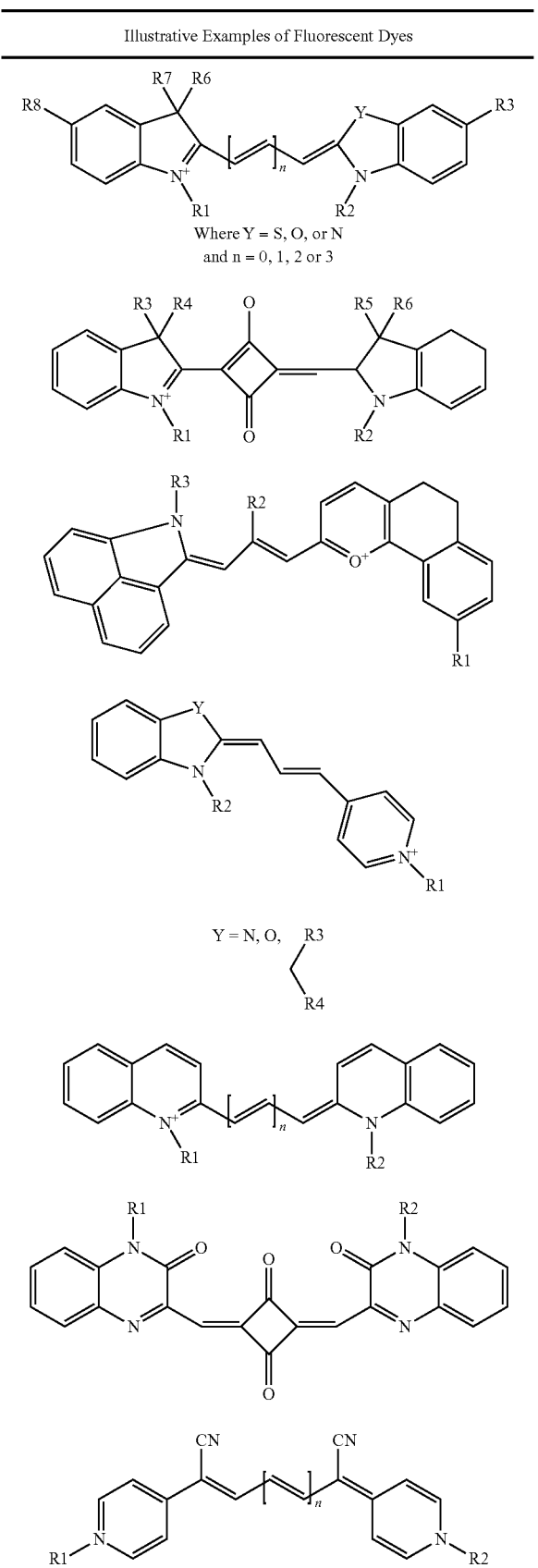
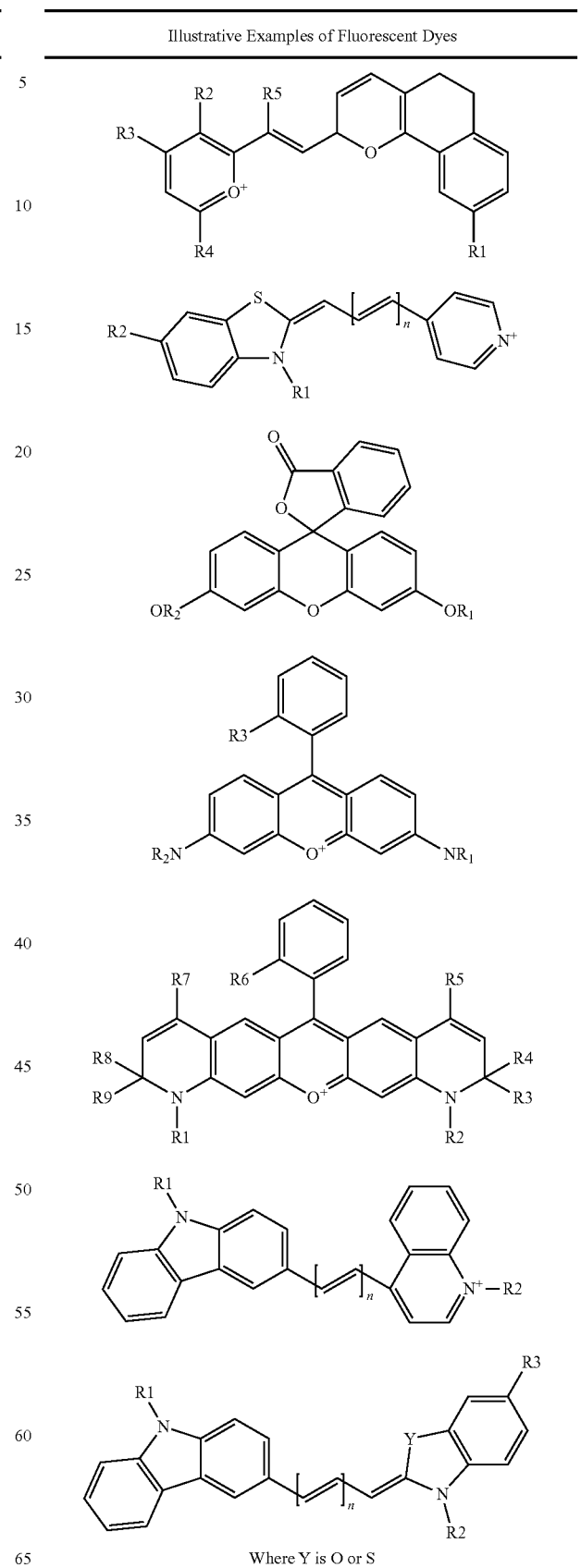

TABLE 2-continued
Illustrative Examples of Fluorescent Dyes
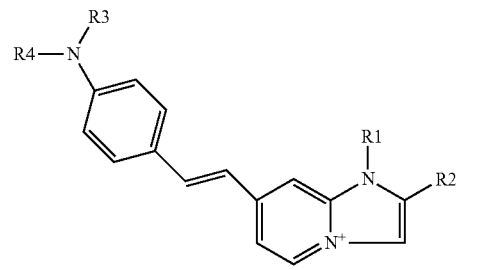
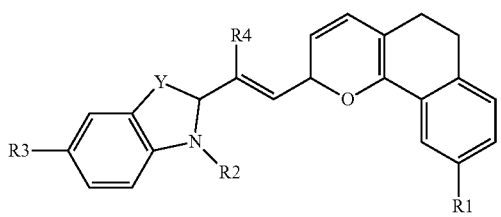
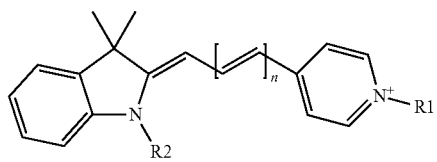
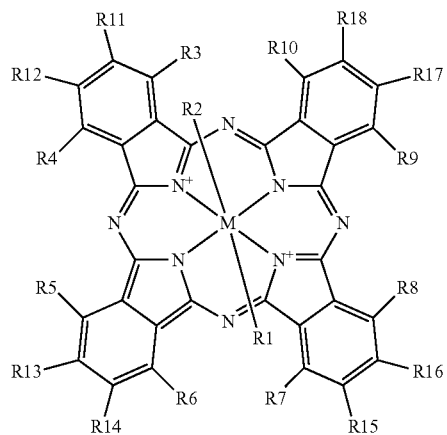
Where M = Silicon, Magnesium, Aluminum, Germanium
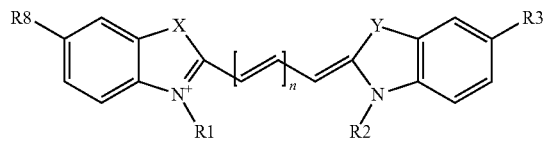
Where X and Y independently = S, N or O
n = 0, 1, 2, or 3
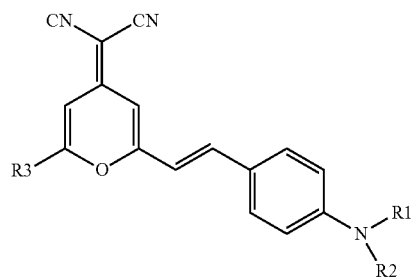
TABLE 2-continued
Illustrative Examples of Fluorescent Dyes
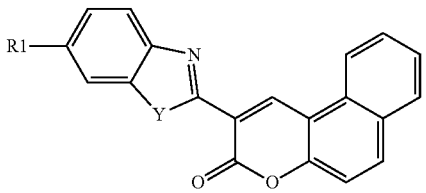
Where Y is O or S
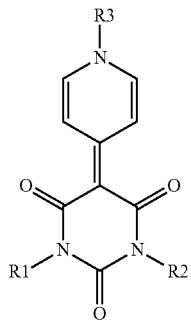
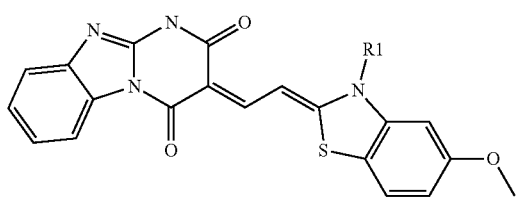
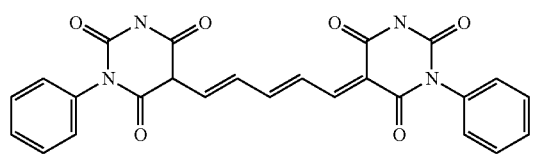 [SMILES: O=C1NC(=O)N(c2ccccc2)C(=O)/C1=C/C=C/C=C/C1C(=O)NC(=O)N(c2ccccc2)C1=O]
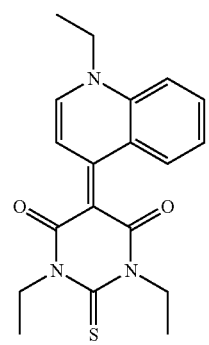 [SMILES: CCN1C(=O)C(=C2C=CN(CC)c3ccccc32)C(=O)N(CC)C1=S]
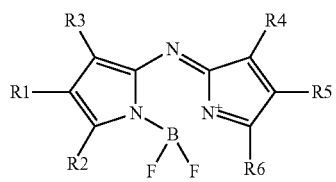

TABLE 2-continued

Illustrative Examples of Fluorescent Dyes

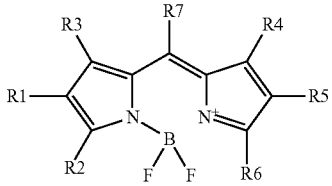

R1-R18 are independently hydrogen, alkyl, alkoxy, alkenyl, cycloalkyl, arylalkyl, acyl, heteroaryl, or halogen, amino or substituted amino.

Dyes further useful for this invention include fluorescent dyes comprising a water dispersible, near-infrared tricarbocyanine, enamine-functionalized dye having a Stokes shift of greater than 50 nm and represented by the following five general formulae:

General Formula I

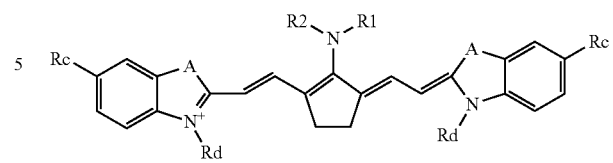

Wherein R1 and R2 are substituted alkyl and may form a ring and at least one of R1 or R2 is a linking group selected from a list of COOH, NH2, maleimide, thiol, isocyanate, isothiocyanate, disulfide, alkynyl, azidoyl, or trialkoxysilane; A is NRa, S, O, Ra—C—Rb, wherein Ra and Rb are substituted or unsubstituted alkyl groups capable of forming a ring; Rc is hydrogen or SO3-, aryl, alkyl, alkoxy, or halogen; Rd is alkyl or (CH2)nSO3- where n=2 to 4, General Formula II

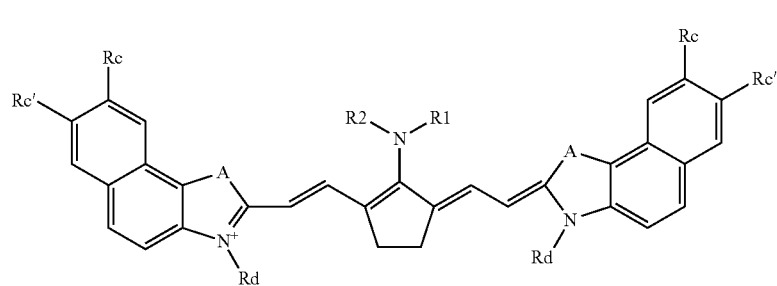

Wherein R1 and R2 are substituted alkyl and are capable of forming a ring, and at least one of R1 or R2 is a linking group selected from a list of COOH, NH2, maleimide, thiol, isocyanate, isothiocyanate, disulfide, alkynyl, azidoyl, or trialkoxysilane; A is NRa, S, O, Ra—C—Rb, wherein Ra and Rb are substituted or unsubstituted alkyl groups capable of forming a ring; Rc is hydrogen or SO3-, aryl, alkyl, alkoxy, or halogen; Rd is alkyl or (CH2)nSO3- where n=2 to 4, General Formula III

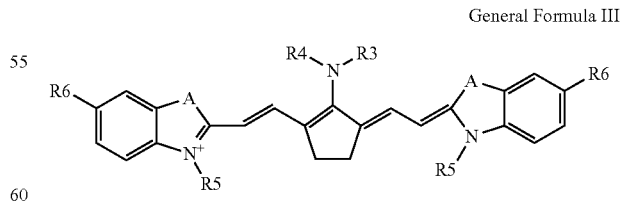

Wherein A is NRa, S, O, Ra—C—Rb; R3, R4, Ra, and Rb are substituted or unsubstituted alkyl capable of joining together to form a ring; R6 is a SO3-; R5 is substituted alkyl and at least one of the substituents is selected from a list of OH, NH2, COOH, maleimide, thiol, isocyante, isothiocyanate, disulfide, alkynyl, azidoyl, or trialkoxysilane;

General Formula IV

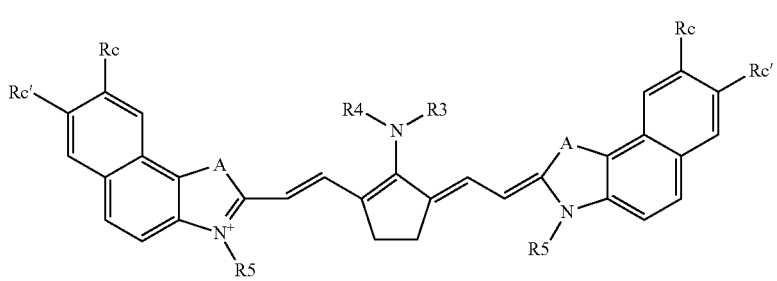

Wherein A is NRa, S, O, Ra—C—Rb; R3, R4, Ra, and Rb are substituted or unsubstituted alkyl capable of joining together to form a ring; at least one of Rc and Rc' is a SO3-; R5 is substituted alkyl and at least one of the substituents is selected from the group consisting of OH, NH2, COOH, maleimide, thiol, isocyante, isothiocyanate, disulfide, alkynyl, azidoyl, or trialkoxysilane; Rc is hydrogen or SO3-, aryl, alkyl, alkoxy, or halogen; and General Formula V

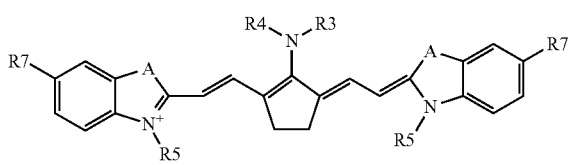

Wherein A is NRa, S, O, Ra—C—Rb; R3, R4, Ra, and Rb are substituted or unsubstituted alkyl capable of joining together to form a ring; R7 is a COOH; R5 is substituted alkyl and contains a SO3- group.

functionalized dye having a Stokes shift of greater than 50 nm and represented by the following two general formulae:

General Formula I

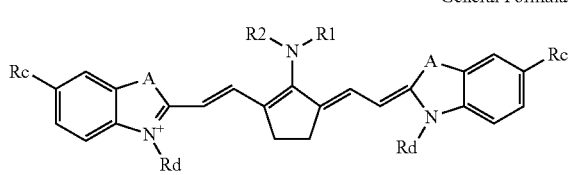

wherein R1 and R2 are substituted alkyl and may form a ring; A is NRa, S, O, Ra—C—Rb, wherein Ra and Rb are substituted or unsubstituted alkyl groups capable of forming a ring; Rc is hydrogen, aryl, alkyl, alkoxy, or halogen; Rd is alkyl chain CH2(n)-CH3 where n=2 to 30, and/or aryl group; a preferred embodiment comprises the case wherein Rd is alkyl where n=11; and General Formula II

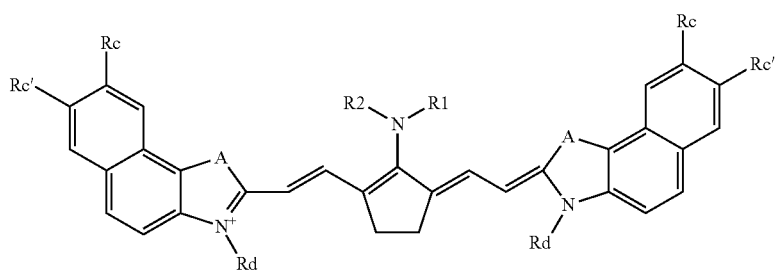

Dyes further useful for this invention include fluorescent dyes having large Stokes shift which are organic solvent soluble and demonstrate insolubility in water. Preferably, when the dyes are loaded into the water soluble latex particle, an increase is observed in quantum yield of fluorescence as compared to the quantum yield of the dye in aqueous solvent. In a preferred embodiment, the fluorescent dye comprises a water dispersible, near-infrared tricarbocyanine, enaminewherein R1 and R2 are substituted alkyl and are capable of forming a ring; A is NRa, S, O, Ra—C—Rb, wherein Ra and Rb are substituted or unsubstituted alkyl groups capable of forming a ring; Rc is hydrogen, aryl, alkyl, alkoxy, or halogen; Rd is alkyl chain CH2(n)-CH3 where n=2 to 30, and/or aryl group.

In a preferred embodiment, the fluorescent dye is represented by the following formula:

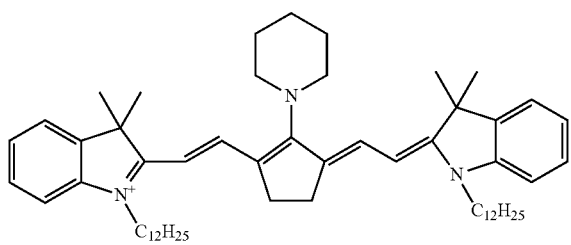

In another preferred embodiment, the fluorescent dye is represented by the following formula:

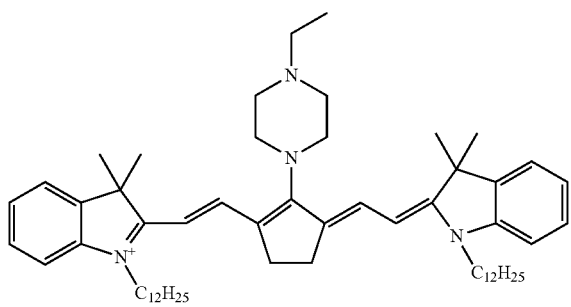

Preferably, the fluorescent dyes utilized with the latex particle are organic solvent soluble and demonstrate insolubility in water. When the dyes are loaded into the water soluble latex particle, an increase is observed in quantum yield of fluorescence as compared to the quantum yield of the dye in aqueous solvent.

The fluorescent dye can be loaded into the latex by a variety of known methods. For example, a solution of the dye in a water-miscible organic solvent can be mixed with the latex, and then the solvent can be removed by evaporation, dilution with water, or dialysis, as described in U.S. Pat. No. 6,706,460, U.S. Pat. No. 4,368,258, U.S. Pat. No. 4,199,363 and U.S. Pat. No. 6,964,844. A solution of the dye in a water-immiscible organic solvent can be combined with the aqueous latex and the mixture subjected to high shear mixing, as described in U.S. Pat. No. 5,594,047. Alternately, the dye can be incorporated during the preparation of the latex. Such a method is described in Journal of Polymer Science Part A: Polymer Chemistry, Vol. 33, p. 2961-2968, 1995 and in Colloid and Polymer Science, vol. 282, p. 119-126, 2003.

The loaded latex particle may be used as an imaging probe for use in animals, as well as other physiological systems. The particle may be used as a diagnostic contrast element or in other in vitro/in vivo, physiological imaging applications. The particle may be provided in an aqueous, biocompatible dispersion.

The described composition can further comprise a biological, pharmaceutical or diagnostic component that includes a targeting moiety that recognizes the specific target cell or other target biological molecules. As used herein "target cells" refers to healthy cells, disease cells, mammalian cell, or plant cells. "Target biological molecules" include, but not limited to, proteins, protein fragments, nucleic acids, or any essential metabolites.

A representative, but non-limiting, list of moieties that can be employed as targeting agents useful with the present compositions is selected from the group consisting of proteins, peptides, aptomers, small organic molecules, toxins, diptheria toxin, pseudomonas toxin, cholera toxin, ricin, concanavalin A, Rous sarcoma virus, Semliki forest virus, vesicular stomatitis virus, adenovirus, transferrin, low density lipoprotein, transcobalamin, yolk proteins, epidermal growth factor, growth hormone, thyroid stimulating hormone, nerve growth factor, calcitonin, glucagon, prolactin, luteinizing hormone, thyroid hormone, platelet derived growth factor, interferon, catecholamines, peptidomimetrics, glycolipids, glycoproteins and polysaccharides. Homologs or fragments of the presented moieties can also be employed. These targeting moieties can be associated with a nanoparticulate and be used to direct the nanoparticle to bind a chosen target. There is no requirement that the entire moiety be used as a targeting moiety. Smaller fragments of these moieties known to interact with a specific receptor or other structure can also be used as a targeting moiety.

An antibody or an antibody fragment represents a class of most universally used targeting moiety that can be linked to a nanolatex. Antibodies may be prepared by any of a variety of techniques known to those of ordinary skill in the art. See, e.g., Harlow and Lane, Antibodies: A Laboratory Manual, Cold Spring Harbor Laboratory Press, 1988. Antibodies can be produced by cell culture techniques, including the generation of monoclonal antibodies or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). A superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, Eur. J. Immunol, 6:511-519, 1976, and improvements thereto.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of "humanized" antibody molecules comprising an antigen-binding site derived from a non-human immunoglobulin have been described (Winter et al. (1991) Nature 349:293-299; Lobuglio et al. (1989) Proc. Nat. Acad. Sci. USA 86:4220-4224. These "humanized" molecules are designed to minimize unwanted immunological response toward rodent antihuman antibody molecules that limits the duration and effectiveness of therapeutic applications of those moieties in human recipients.

The recognition moiety can further comprise a sequence of peptides or nucleic acids that can be recognized by a select target. The peptides and nucleic acids can be selected from a sequence known in the art for their ability to bind to a chosen target, or to be selected from combinatorial peptide or nucleic acid libraries for their ability to bind a chosen target.

Vitamins and other essential minerals and nutrients can be utilized as targeting moiety to enhance the binding of nanolatex particle to a target. In particular, a vitamin ligand can be selected from the group consisting of folate, folate receptor-binding analogs of folate, and other folate receptor-binding ligands, biotin, biotin receptor-binding analogs of biotin and other biotin receptor-binding ligands, riboflavin, riboflavin receptor-binding analogs of riboflavin and other riboflavin receptor-binding ligands, and thiamin, thiamin receptor-binding analogs of thiamin and other thiamin receptor-binding ligands.

Since not all natural cell membranes possess biologically active biotin or folate receptors, use of the described compositions in-vitro on a particular cell line can involve altering or otherwise modifying that cell line first to ensure the presence of biologically active biotin or folate receptors. Thus, the number of biotin or folate receptors on a cell membrane can be increased by growing a cell line on biotin or folate deficient substrates to promote biotin and folate receptor production, or by expression of an inserted foreign gene for the protein or apoprotein corresponding to the biotin or folate receptor.

The recognition moiety can further comprise a sequence that is subject to enzymatic or electrochemical cleavage. The recognition moiety can thus comprise a sequence that is susceptible to cleavage by enzymes present at various locations inside a cell, such as proteases or restriction endonucleases (e.g. DNAse or RNAse).

For cell targeting, a cell surface recognition sequence is not a must-have requirement. Thus, although a cell surface receptor targeting moiety can be useful for targeting a given cell type, or for inducing the association of a described nanoparticle with a cell surface, there is no requirement that a cell surface receptor targeting moiety be present on the surface of a nanolatex particle.

To assemble the biological, pharmaceutical or diagnostic components to a described nanoparticulate carrier, the components can be associated with the nanoparticle carrier through a linkage. By "associated with", it is meant that the component is carried by the nanoparticle, for example the surface of the nanoparticle. The component can be dissolved and incorporated in the particle non-covalently. A preferred method of associating the component is by covalent bonding through the amine function on the surface.

Generally, any manner of forming a linkage between a targeting moiety of interest and a nanolatex particulate carrier can be utilized. This can include covalent, ionic, or hydrogen bonding of the ligand to the exogenous molecule, either directly or indirectly via a linking group. The linkage is typically formed by covalent bonding of the targeting moiety, biological, pharmaceutical or diagnostic component to the nanoparticle carrier through the formation of amide, ester or imino bonds between acid, aldehyde, hydroxy, amino, or hydrazo groups on the respective components of the complex. Art-recognized biologically labile covalent linkages such as imino bonds and so-called "active" esters having the linkage —COOCH, —O—O— or —COOCH are preferred. Hydrogen bonding, e.g., that occurring between complementary strands of nucleic acids, can also be used for linkage formation.

In a preferred embodiment of this invention, the targeting moiety is covalently attached to the reactive group at then end of the polyethylene glycol macromonomer. The covalent linkage used will be dependent on the reactive group at the end of the polyethylene glycol. For example, if the reactive group is an amine, it can react with an activated carboxylic acid derivative on the targeting moiety (such as an N-hydroxysuccinimidyl ester) to form an amide bond. If the reactive group is a vinylsulfone, it can react with a primary amine on the targeting moiety to afford a secondary amine linkage.

The examples are offered to illustrate, but not to limit, the claimed invention.

Example 1

TABLE 3

Structure of Dyes

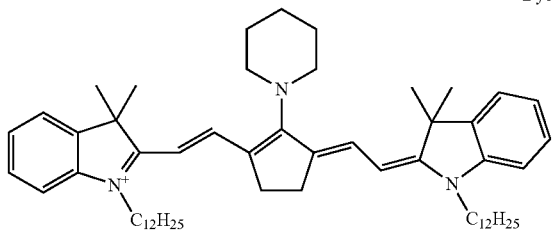

Dye 1

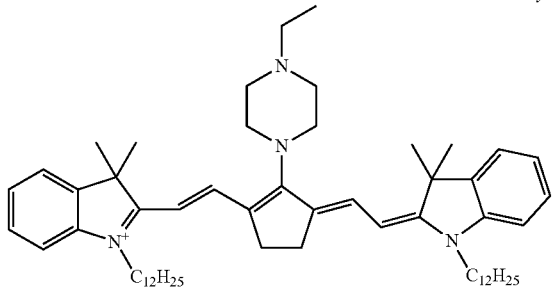

Dye 2

General Synthetic Scheme, Dye 1

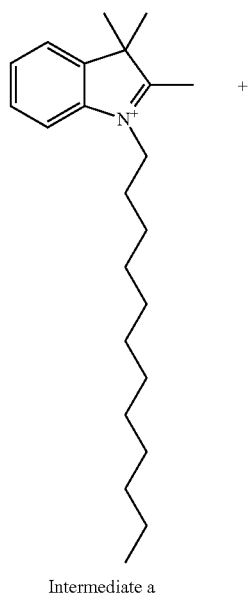 [SMILES: CCCCCCCCCCCC[N+]1=C(C)C(C)(C)c2ccccc21]

Intermediate a

TABLE 3-continued
Structure of Dyes
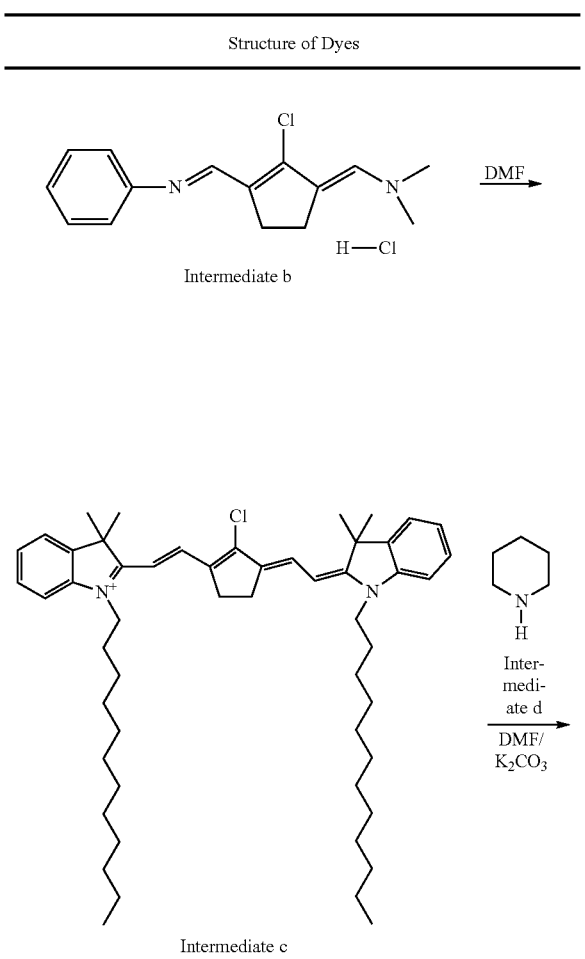
Intermediate b
Intermediate c
Cmpd 1
TABLE 3-continued
Structure of Dyes
General Synthetic Scheme, Dye 2
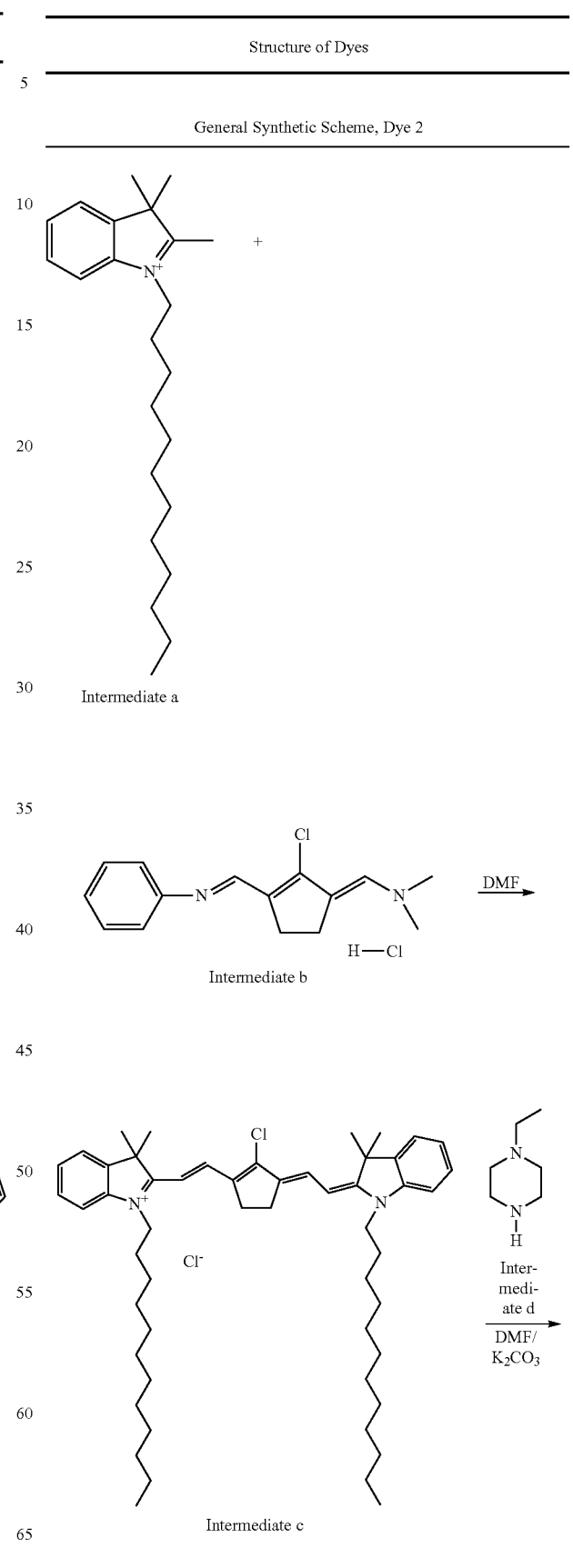
Intermediate a
Intermediate b
Intermediate c

TABLE 3-continued

Structure of Dyes

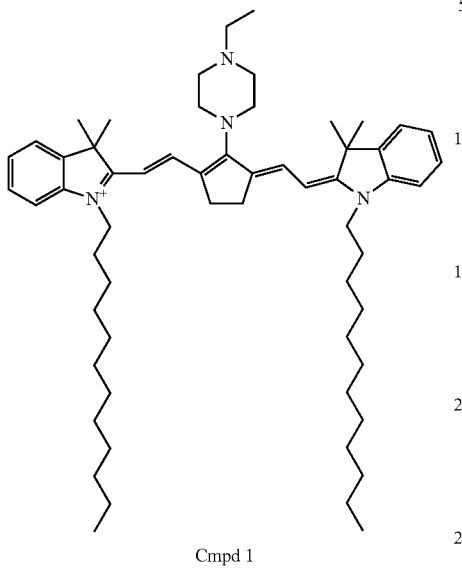

Cmpd 1

Synthetic Procedure 1 for Chloro Intermediate Dye C

This dye was prepared by the procedure above using 2,3,3-trimethyl-1-doceyl-3H-Indolium perchlorate (86 mg, 0.0273 mol) and the dianil (30 mg, 0.0101 mol) in 0.1 mL of acetic anhydride and 1 mL of DMF containing triethylamine (80 μL). The reaction was carried out for 60 minutes at 70° C., cooled to 25° C. and poured into 10 mL of ice water with vigorous stirring. The water was decanted from the oily product then chromatographed on silica gel eluting with 90/10 methylene chloride-methanol. Evaporation of the solvent afforded pure dye (100 mg). Mass spec MW=778.5=M+H$^+$, λmax=780 nm in methanol/H2O(HPLC Diode Array Detector).

Synthesis of Dye 1

This dye was prepared using above chloro dye (50 mg, 0.0615 mmol) and piperidine (28 μL, 20.3 mg, 0.24 mmol) in 0.5 mL of DMF containing triethylamine (80 μL, 0.058 g, 0.58 mmol). The reaction was carried out for 60 minutes at 80° C., cooled to 25° C. and poured into 10 mL of ice water with vigorous stirring. The water was decanted from the oily product then chromatographed on silica gel eluting with 90/10 methylene chloride-methanol. Evaporation of the solvent afforded pure dye (20 mg). Mass Spec=826.6=M+H, λmax=685 nm in methanol (in HPLC/H20 diode array detector).

Synthesis of Dye 2

This dye was prepared using above chloro dye (50 mg, 0.0615 mmol) and N-ethyl-piperazine 29 μL, 26 mg, 0.23 mmol) in 0.5 mL of DMF containing triethylamine (80 μl). The reaction was carried out for 60 minutes at 80° C., cooled to 25° C. and poured into 10 mL of ice water with vigorous stirring. The water was decanted from the oily product then chromatographed on silica gel eluting with 90/10 methylene chloride-methanol. Evaporation of the solvent afforded pure dye (20 mg). Mass Spec=855.7=M+H, λmax=697 nm in methanol (in HPLCdiode array detector).

Example 2

Preparation of Amine-Terminated Polyethylene Glycol Macromonomer

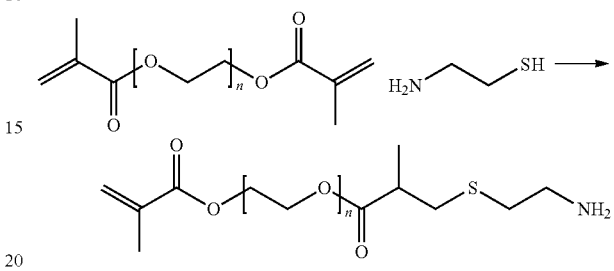

Polyethyleneglycol dimethacrylate (Aldrich, Mn=875, 335 g) was mixed with 100 ml of methanol and treated with cysteamine (Aldrich, 5.8 g) and diisopropylethylamine (Hunigs base) and was stirred at RT for 2 days and concentrated using a rotary evaporator. The residue was taken up in 1 L of ethyl acetate and extracted with aqueous 10% HCl. The aqueous layer was collected and made basic by the addition of 50% aqueous sodium hydroxide followed by extraction with ethyl acetate. The organic layer was dried over MgSO$_4$, filtered and concentrated. The residue was taken up in anhydrous diethyl ether and treated with gaseous HCl and allowed to stand. The ether was decanted to leave a dark blue oil. This material was washed with fresh diethyl ether, which was decanted. The dark blue oil was concentrated using a rotary evaporator to give 37 g of the desired product as the hydrochloride salt.

$^1$H-NMR (300 MHZ, CDCl$_3$): D 1.18 (d, 3H), 1.93 (bs, 3H), 2.04 (bs, 2H), 2.43-2.77 (bm, 7H), 3.6-3.7 (vbs, —CH$_2$CH$_2$O—), 3.73 (bt, 2H), 3.29 (bt, 2H), 5.56 (bs, 1H), 6.12 (bs, 1H).

Example 3

Preparation of Nanolatex 1 Comprised of Methoxyethyl Methacrylate (45% w/w), Divinylbenzene (4%), Ethylstyrene (1%), and Poly(Ethylene Glycol) Monomethyl Ether Methacrylate (50%)

A 500 ml 3-neck round bottomed flask was modified with Ace #15 glass threads at the bottom and a series of adapters allowing connection of 1/16 inch ID Teflon tubing. The flask (hereafter referred to as the "header" flask) was outfitted with a mechanical stirrer, rubber septum with syringe needle nitrogen inlet. The header flask was charged with methoxyethyl methacrylate (5.63 g), divinylbenzene (0.63 g, mixture of isomers, 80% pure with remainder being ethylstyrene isomers), poly(ethylene glycol) monomethyl ether methacrylate (6.25 g, M$_n$, =1100), cetylpyridinium chloride (0.31 g), 2,2'-azobis(N,N'-dimethyleneisobutyramidine) dihydrochloride (0.06 g), sodium bicarbonate (0.06 g) and distilled water (78.38 g). A 1 L 3-neck round bottomed flask outfitted with a mechanical stirrer, reflux condenser, nitrogen inlet, and rubber septum (hereafter referred to as the "reactor") was charged with 2,2'-azobis(N,N'-dimethyleneisobutyramidine) dihydrochloride (0.06 g), sodium bicarbonate (0.06 g), and distilled water (159.13 g). Both the header and reactor contents were stirred until homogeneous and were bubble degassed with nitrogen for 20 minutes. The reactor flask was placed in a thermostatted water bath at 60° C. and the header contents were added to the reactor over two hours using a model QG6 lab pump (Fluid Metering Inc. Syossett, N.Y.). The reaction mixture was then allowed to stir at 60° C. for 16 hours. The reaction mixture was then dialyzed for 48 hours using a 3.5K cutoff membrane in a bath with continual water replenishment. 286.0 g of a colorless dispersion of 2.64% solids was obtained. The volume average diameter was found to be 10.8 nm with a coefficient of variation of 0.25 by quasi-elastic light scattering (QELS). QELS was performed using a Nanotrac Ultrafine Particle Analyzer (Microtrac Inc. Montgomeryville, Pa.) at 3-5% solids.

Example 4

Preparation of Nanolatex 2 (Ion-Exchanged Replicate Run of Nanolatex 1)

This nanolatex was prepared using the same method as described in Example 2. The header contained methoxyethyl methacrylate (22.50 g), divinylbenzene (2.50 g, mixture of isomers, 80% pure with remainder being ethylstyrene isomers), poly(ethylene glycol) monomethyl ether methacrylate (22.50 g, $M_n$=1100), 2,2'-azobis(N,N'-dimethyleneisobutyramidine) dihydrochloride (0.25 g), sodium bicarbonate (0.25 g), and distilled water (313.50 g). The reactor contents were composed of distilled water (636.50 g), 2,2'-azobis(N,N'-dimethyleneisobutyramidine) dihydrochloride (0.25 g), and sodium bicarbonate (0.25 g). 771 g of a clear dispersion of 5.59% solids was obtained. The volume average diameter was found to be 10.4 nm with a coefficient of variation of 0.27 by quasi-elastic light scattering. 200 g of this latex was dialyzed for 48 hours using a 3.5K cutoff membrane. 50 g of the dialyzed latex was then stirred over 15 cc Dowex 50W×4 ion exchange resin (converted to the sodium form and washed 3× with distilled water) to afford an ion exchanged dispersion of 3.85% solids.

Example 5

Preparation of Nanolatex 3 (Large Scale Replicate Run of Nanolatex 1)

This nanolatex was prepared using the same method as described in Example 2. The header contained methoxyyethyl methacrylate (45.00 g), divinylbenzene (5.00 g, mixture of isomers, 80% pure with remainder being ethylstyrene isomers), poly(ethylene glycol) monomethyl ether methacrylate (50.00 g, $M_n$=1100), 2,2'-azobis(N,N'-dimethyleneisobutyramidine) dihydrochloride (0.50 g), sodium bicarbonate (0.50 g), and distilled water (627.00 g). The reactor contents were composed of distilled water (1273.00 g), 2,2'-azobis(N,N'-dimethyleneisobutyramidine) dihydrochloride (0.50 g), and sodium bicarbonate (0.50 g). The latex was subjected to ultrafiltration using an Amicon LP1 diafiltrations system (Millipore Inc) with a 30K cutoff spiral wound cartridge. After 8 turnovers against distilled water, the latex was treated with ~600 cc Dowex 50W×4 ion exchange resin (converted to the sodium form and washed 3× with distilled water) to afford an ion exchanged dispersion of 5.76% solids. The volume average diameter was found to be 12.0 nm with a coefficient of variation of 0.28 by quasi-elastic light scattering.

Example 6

Preparation of Nanolatex 4 Comprised of Methoxyethyl Methacrylate (45% w/w), Divinylbenzene (4%), Ethylstyrene (1%), Poly(Ethylene Glycol) Monomethyl Ether Methacrylate (45%), and Sodium Styrenesulfonate (5%)

This nanolatex was prepared using the same method as described in Example 2. The header contained methoxyyethyl methacrylate (22.50 g), divinylbenzene (2.50 g, mixture of isomers, 80% pure with remainder being ethylstyrene isomers), poly(ethylene glycol) monomethyl ether methacrylate (22.50 g, $M_n$=1100), sodium persulfate (0.50 g), sodium bicarbonate (0.25 g), and distilled water (313.50 g). The reactor contents were composed of distilled water (636.50 g), sodium metabisulfite (0.36 g), and sodium bicarbonate (0.25 g). 759 g of a clear dispersion of 4.94% solids was obtained. The volume average diameter was found to be 22.2 nm with a coefficient of variation of 0.25 by quasi-elastic light scattering. 200 g of this latex was dialyzed for 48 hours using a 3.5K cutoff membrane to afford 292 g of a dispersion of 3.24% solids.

Example 7

Preparation of Nanolatex 5 Comprised of Methoxyethyl Methacrylate (45% w/w), Divinylbenzene (4%), Ethylstyrene (1%), Poly(Ethylene Glycol) Monomethyl Ether Methacrylate (45%), and Methacrylic Acid (5%)

This nanolatex was prepared using the same method as described in Example 2. The header contained methoxyyethyl methacrylate (112.5 g), divinylbenzene (1.25 g, mixture of isomers, 80% pure with remainder being ethylstyrene isomers), poly(ethylene glycol) monomethyl ether methacrylate (11.25 g, $M_n$=1100), 2,2'-azobis(N,N'-dimethyleneisobutyramidine) dihydrochloride (0.13 g), cetylpyridinium chloride (0.63), and distilled water (156.75 g). The reactor contents were composed of distilled water (318.25 g), 2,2'-azobis(N,N'-dimethyleneisobutyramidine) dihydrochloride (0.13 g), and cetylpyridinium chloride (1.88 g). The latex was twice stirred for 1 hour with 200 cc Dowex 88 ion exchange resin and dialyzed for 48 hours using a 3.5K cutoff membrane to afford clear latex of 4.39% solids. The volume average diameter was found to be 10.98 nm with a coefficient of variation of 0.29 by quasi-elastic light scattering.

Example 8

Preparation of Nanolatex 6 Comprised of Methoxyethyl Methacrylate (45% w/w), Divinylbenzene (4%), Ethylstyrene (1%), and Poly(Ethylene Glycol) Monomethyl Ether Methacrylate (50%)

This nanolatex was prepared using the same method as described in Example 2. The header contained methoxyethyl methacrylate (5.63 g), divinylbenzene (0.63 g, mixture of isomers, 80% pure with remainder being ethylstyrene isomers), poly(ethylene glycol) monomethyl ether methacrylate (6.25 g, $M_n$=1100), 2,2'-azobis(N,N'-dimethyleneisobutyramidine) dihydrochloride (0.06 g), cetylpyridinium chloride (0.31), sodium bicarbonate (0.06 g) and distilled water (78.38 g). The reactor contents were composed of distilled water (159.13 g), 2,2'-azobis(N,N'-dimethyleneisobutyramidine)

dihydrochloride (0.06 g), sodium bicarbonate (0.06 g) and cetylpyridinium chloride (0.94 g). The latex was treated twice with 100 cc Dowex 88 ion exchange resin and dialyzed for 48 hours using a 14K cutoff membrane to afford to afford 312 g of a clear latex of 3.26% solids. The volume average diameter was found to be 20.89 nm with a coefficient of variation of 0.24 by quasi-elastic light scattering.

Example 9

Preparation of Nanolatex 7 Comprised of Styrene (70% w/w), Divinylbenzene (4%), Ethylstyrene (1%), and Poly(Ethylene Glycol) Monomethyl Ether Methacrylate (25%)

This nanolatex was prepared using the same method as described in Example 2. The header contained styrene (8.75 g), divinylbenzene (0.63 g, mixture of isomers, 80% pure with remainder being ethylstyrene isomers), poly(ethylene glycol) monomethyl ether methacrylate (3.13 g, $M_n$=1100), 2,2'-azobis(N,N'-dimethyleneisobutyramidine) dihydrochloride (0.06 g), cetylpyridinium chloride (0.31), and distilled water (78.38 g). The reactor contents were composed of distilled water (159.13 g), 2,2'-azobis(N,N'-dimethyleneisobutyramidine) dihydrochloride (0.63 g), and cetylpyridinium chloride (0.94 g). The latex was dialyzed for 48 hours using a 3.5K cutoff membrane to afford 251 g of a clear latex of 3.38% solids. The volume average diameter was found to be 12.82 nm with a coefficient of variation of 0.36 by quasi-elastic light scattering.

Example 10

Preparation of Nanolatex 8 Comprised of Styrene (45% w/w), Divinylbenzene (4%), Ethylstyrene (1%), and Poly(Ethylene Glycol) Monomethyl Ether Methacrylate (50%)

This nanolatex was prepared using the same method as described in Example 2. The header contained styrene (11.25 g), divinylbenzene (1.25 g, mixture of isomers, 80% pure with remainder being ethylstyrene isomers), poly(ethylene glycol) monomethyl ether methacrylate (12.50 g, $M_n$=1100), 2,2'-azobis(N,N'-dimethyleneisobutyramidine) dihydrochloride (0.13 g), cetylpyridinium chloride (0.31), sodium bicarbonate (0.13 g) and distilled water (156.75 g). The reactor contents were composed of distilled water (318.25 g), 2,2'-azobis(N,N'-dimethyleneisobutyramidine) dihydrochloride (0.13 g), sodium bicarbonate (0.13 g) and cetylpyridinium chloride (0.94 g). The latex was dialyzed for 48 hours using a 3.5K cutoff membrane and treated with 250 cc Dowex 88 ion exchange resin to afford to afford 561.23 g of a clear latex of 4.08% solids. The volume average diameter was found to be 13.22 nm with a coefficient of variation of 0.19 by quasi-elastic light scattering.

Example 11

Preparation of Nanolatex 9 Comprised of Methyl Methacrylate (45% w/w), Divinylbenzene (4%), Ethylstyrene (1%), and Poly(Ethylene Glycol) Monomethyl Ether Methacrylate (50%)

This nanolatex was prepared using the same method as described in Example 2. The header contained methyl methacrylate (11.25 g), divinylbenzene (1.25 g, mixture of isomers, 80% pure with remainder being ethylstyrene isomers), poly(ethylene glycol) monomethyl ether methacrylate (12.50 g, $M_n$=1100), 2,2'-azobis(N,N'-dimethyleneisobutyramidine) dihydrochloride (0.13 g), cetylpyridinium chloride (0.31), sodium bicarbonate (0.13 g) and distilled water (156.75 g). The reactor contents were composed of distilled water (318.25 g), 2,2'-azobis(N,N'-dimethyleneisobutyramidine) dihydrochloride (0.13 g), sodium bicarbonate (0.13 g) and cetylpyridinium chloride (0.94 g). The latex was dialyzed for 48 hours using a 3.5K cutoff membrane and treated with 250 cc Dowex 88 ion exchange resin to afford to afford 610.25 g of a clear latex of 3.74% solids. The volume average diameter was found to be 13.30 nm with a coefficient of variation of 0.18 by quasi-elastic light scattering.

Example 12

Preparation of Nanolatex 10 Comprised of Butyl Acrylate (45% w/w), Divinylbenzene (4%), Ethylstyrene (1%), and Poly(Ethylene Glycol) Monomethyl Ether Methacrylate (50%)

This nanolatex was prepared using the same method as described in Example 2. The header contained butyl acrylate (5.63 g), divinylbenzene (0.63 g, mixture of isomers, 80% pure with remainder being ethylstyrene isomers), poly(ethylene glycol) monomethyl ether methacrylate (6.25 g, $M_n$=1100), 2,2'-azobis(N,N'-dimethyleneisobutyramidine) dihydrochloride (0.06 g), cetylpyridinium chloride (0.31), sodium bicarbonate (0.06 g) and distilled water (78.38 g). The reactor contents were composed of distilled water (159.13 g), 2,2'-azobis(N,N'-dimethyleneisobutyramidine) dihydrochloride (0.06 g), sodium bicarbonate (0.06 g) and cetylpyridinium chloride (0.94 g). The latex was dialyzed for 48 hours using a 14K cutoff membrane to afford to afford 263 g of a clear latex of 4.32% solids. The volume average diameter was found to be 24.56 nm with a coefficient of variation of 0.29 by quasi-elastic light scattering.

Example 13

Loading of Nanolatex 1 with Dye 1

A dye solution of ~0.1% was prepared by dissolving 0.0315 g of Dye 1 in 30.545 g of tetrahydrofuran. A 3.2378 g portion of the dye solution was added to a glass vial, followed by a 10.5489 g of Nanolatex 1. The tetrahydrofuran was removed with a small stream of nitrogen over a period of 8-24 hours with stirring. A blue loaded latex LL-1A of 4.27% solids was afforded. Three additional samples with higher loading levels (LL-1B, 1C, 1D) were prepared in an identical manner using the reagent quantities in the table below. Ex/Em: 703 nm/802 nm. FIG. 1 shows the Fluorescence image of dilution series from Loading of Nanolatex 1 with Dye 1.

TABLE 4

Loading of Nanolatex 1 with Dye 1

| Loaded latex designation | Dye solution (g) | Nanolatex (g) | Final weight (g) | Conc. Dye in solid latex (mol/L) | Final % solids (% w/w) |
|---|---|---|---|---|---|
| LL-1A | 3.2378 | 10.5489 | 8.5368 | $4.19 \times 10^{-4}$ | 4.27 |
| LL-1B | 4.6524 | 10.1257 | 8.8755 | $5.78 \times 10^{-4}$ | 4.10 |

TABLE 4-continued

Loading of Nanolatex 1 with Dye 1

| Loaded latex designation | Dye solution (g) | Nanolatex (g) | Final weight (g) | Conc. Dye in solid latex (mol/L) | Final % solids (% w/w) |
|---|---|---|---|---|---|
| LL-1C | 6.2478 | 10.1725 | 9.0253 | $7.65 \times 10^{-4}$ | 3.95 |
| LL-1D | 7.7532 | 10.2548 | 8.9852 | $9.66 \times 10^{-4}$ | 4.05 |

Example 14

Loading of Nanolatex 1 with Dye 2

Figure 2:
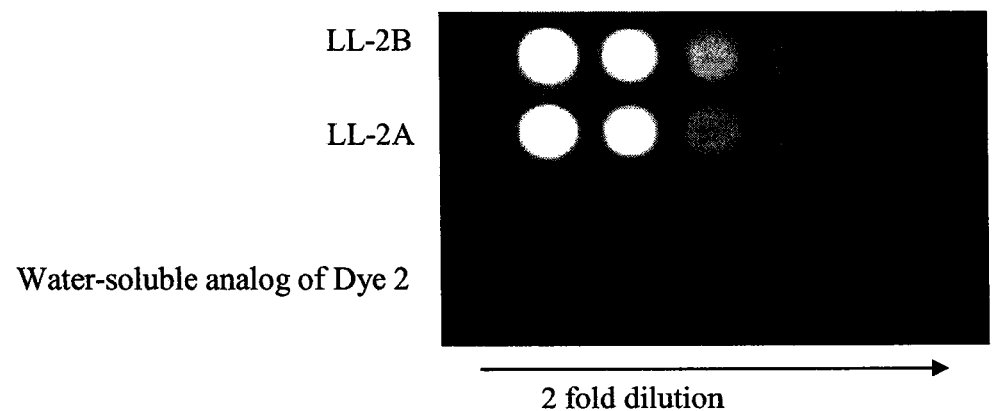
FIG. 2 shows a fluorescence image of dilution series from loading of Nanolatex 1 with Dye 2.

A dye solution of ~0.1% was prepared by dissolving 0.0318 g of Dye 2 in 30.653 g of tetrahydrofuran. A 3.0378 g portion of the dye solution was added to a glass vial, followed by a 10.3289 g of Nanolatex 1. The tetrahydrofuran was removed with a small stream of nitrogen over a period of 8-24 hours with stirring. A blue loaded latex LL-2A of 4.00% solids was afforded. One additional sample (LL-2B) was prepared in an identical manner using the reagent quantities in the table below. Ex/Em: 711 nm/778 nm. FIG. 2 shows the fluorescence image of dilution series from Loading of Nanolatex 1 with Dye 2.

TABLE 5

Loading of Nanolatex 1 with Dye 2

| Loaded latex designation | Dye solution (g) | Nanolatex (g) | Final weight (g) | Conc. Dye in solid latex (mol/L) | Final % solids (% w/w) |
|---|---|---|---|---|---|
| LL-2A | 3.2596 | 10.1023 | 8.2538 | $4.58 \times 10^{-4}$ | 4.51 |
| LL-2B | 4.6357 | 10.0676 | 9.0253 | $5.89 \times 10^{-4}$ | 3.92 |

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

The invention claimed is:

1. A nanolatex particle comprising a latex material made from a mixture represented by formula:

(X)$m$-(Y)$n$-(Z)$o$-(W)$p$ wherein Y is at least one monomer with at least two ethylenically unsaturated chemical functionalities; Z is at least one polyethylene glycol macromonomer with an average molecular weight of between 300 and 10,000; W is an ethylenic monomer different from X, Y, or Z; and X is at least one water insoluble, alkoxethyl containing monomer represented by formula:

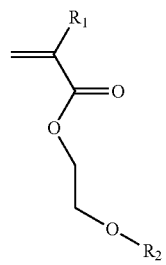

wherein R1 is a radical selected from the group consisting of methyl and hydrogen, and R2 is a radical selected from the group consisting of an alkyl group and an aryl group; and m, n, o, and p are weight percent ranges of each component monomer, wherein m ranges between 40-90 percent by weight, n ranges between 1-10 percent by weight, o ranges between 20-60 percent by weight, and p is up to 10 percent by weight; and wherein said particle is loaded with a fluorescent dye compound, wherein the fluorescent dye compound is a water dispersible, near-infrared tricarbocyanine, enamine-functionalized dye compound having a Stokes shift of greater than 50 nm and represented by at least one of the following two general formulae General Formula I

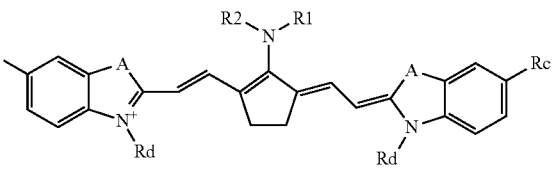

wherein R1 and R2 are substituted alkyl and may together form a ring; A is NRa, S, O, Ra-C-Rb, wherein Ra and Rb are substituted or unsubstituted alkyl groups capable of forming a ring; Rc is hydrogen, aryl, alkyl, alkoxy, or halogen; Rd is alkyl chain CH2(n)-CH3 where n=2 to 30, and/or aryl group;

General Formula II

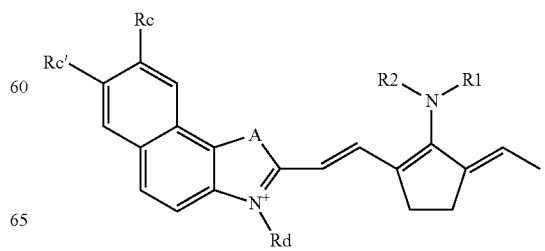

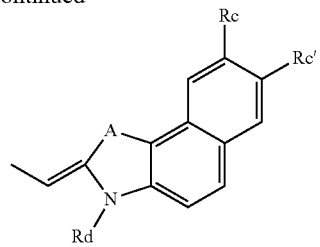

wherein R1 and R2 are substituted alkyl and may together form a ring; A is NRa, S, O, Ra-C-Rb, wherein Ra and Rb are substituted or unsubstituted alkyl groups capable of forming a ring; Rc is hydrogen, aryl, alkyl, alkoxy, or halogen; Rd is alkyl chain CH2(n)-CH3 where n=2 to 30, and/or aryl group.

2. The nanolatex particle of claim 1, wherein the water dispersible, near-infrared tricarbocyanine, enamine-functionalized dye compound having a Stokes shift of greater than 50 nm is represented by the following general formula:

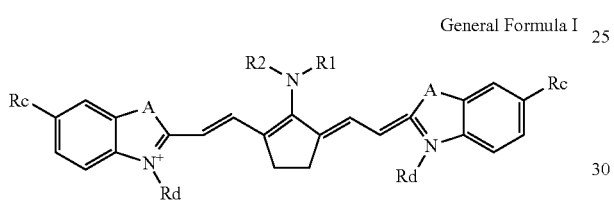

General Formula I wherein R1 and R2 are substituted alkyl and may together form a ring; A is NRa, S, O, Ra-C-Rb, wherein Ra and Rb are substituted or unsubstituted alkyl groups capable of forming a ring; Rc is hydrogen, aryl, alkyl, alkoxy, or halogen; Rd is alkyl chain CH2(n)-CH3 where n=2 to 30, and/or aryl group.

3. The nanolatex particle of claim 1, wherein the water dispersible, near-infrared tricarbocyanine, enamine-functionalized dye compound having a Stokes shift of greater than 50 nm is represented by the following general formula:

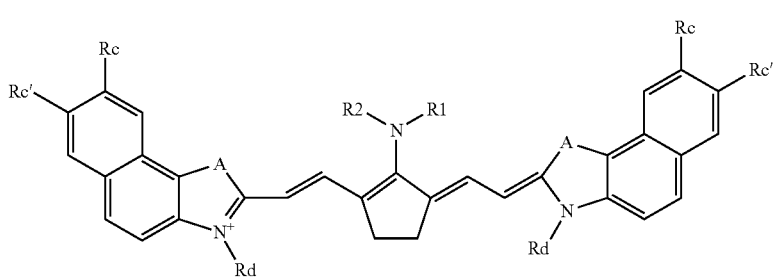

General Formula II wherein R1 and R2 are substituted alkyl and may together form a ring; A is NRa, S, O, Ra-C-Rb, wherein Ra and Rb are substituted or unsubstituted alkyl groups capable of forming a ring; Re is hydrogen, aryl, alkyl, alkoxy, or halogen; Rd is alkyl chain CH2(n)-CH3 where n=2 to 30, and/or aryl group.

4. The nanolatex particle of claim 2, wherein the water dispersible, near-infrared tricarbocyanine, enamine-functionalized dye compound having a Stokes shift of greater than 50 nm is represented by the following formula:

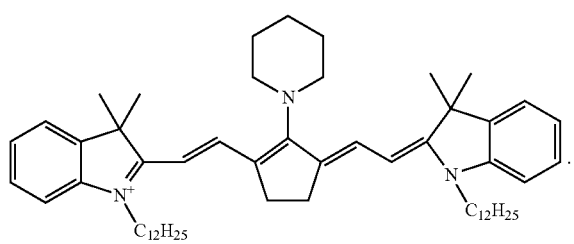

5. The nanolatex particle of claim 2, wherein the water dispersible, near-infrared tricarbocyanine, enamine-functionalized dye compound having a Stokes shift of greater than 50 nm is represented by the following formula:

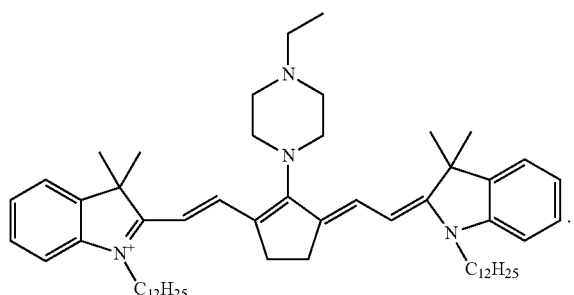

6. The nanolatex particle of claim 1, wherein said Z monomer is a polyethylene glycol backbone chain comprising at least one functional end group.

7. The nanolatex particle of claim 1, wherein Z is a polyethylene glycol macromonomer represented by a general formula:

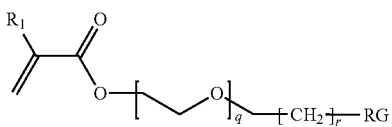

wherein R1 is a radical selected from the group consisting of hydrogen and methyl; q is 10-200; r is O-10; and RG is a reactive chemical functionality selected from the group consisting of: alcohol; thiol; carboxylic acid; primary amine; secondary amine; vinylsulfonyl; aldehyde; epoxy; hydrazide; succinimidyl ester; maleimide; acetate; substituted carbamyl; substituted phosphate; sulfonate a-halo carbonyl moiety; iodoacetyl; isocyanate; isothiocyanate; and aziridine.

8. The nanolatex particle of claim 1, wherein Z is a polyethylene glycol macromonomer represented by a general formula:

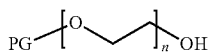

wherein n is greater than 4 and PG is a polymerizable group.

9. The nanolatex particle of claim 1, wherein said polyethylene glycol macromonomer is a polyethylene glycol derivative represented by formula:

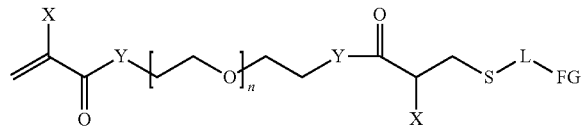

wherein X is selected from the group consisting of: $CH_3$ and H; Y is selected from the group consisting of O, NR, and S; L is selected from the group consisting of: a linking group and spacer; FG is a functional group; and n is greater than or equal to 4 and less than or equal to 1000.

10. The nanolatex particle of claim 1, further comprising a targeting agent.

11. The nanolatex particle of claim 1, further comprising a biomolecule.

12. The nanolatex particle of claim 1, further comprising a diagnostic agent.

13. The nanolatex particle of claim 1, further comprising a therapeutic agent.

14. The nanolatex particle of claim 1, wherein said nanolatex particle is biocompatible.

15. The nanolatex particle of claim 1, wherein said fluorescent dye compound is organic solvent soluble and insoluble in water.

16. The nanolatex particle of claim 1, wherein X is methoxyethyl methacrylate.

17. The nanolatex particle of claim 1, wherein m ranges between 45-60 percent by weight.

18. The nanolatex particle of claim 1, wherein; n ranges between 2-6 percent by weight.

19. The nanolatex particle of claim 1, wherein o ranges between 40-50 percent by weight.

20. The nanolatex particle of claim 1, wherein Y is a monomer containing at least two ethylenically unsaturated chemical functionalities.

21. The nanolatex particle of claim 20, wherein said functionalities are selected from the group consisting of: vinyl groups; acrylates; methacrylates; acrylamides; methacrylamides; allyl groups; vinyl ethers; and vinyl esters.

22. The nanolatex particle of claim 20, wherein said Y monomer is selected from the group consisting of: aromatic divinyl compounds, such as divinylbenzene, divinylnaphthalene, and derivatives thereof; diethylene carboxylate esters and amides, such as ethylene glycol dimethacrylate, diethylene glycol diacrylate, 1,4 butanediol diacrylate, 1,4 butanediol dimethacrylate, 1,3 butylene glycol diacrylate, 1,3 butylene glycol dimethacrylate, cyclohexane dimethanol diacrylate, cyclohexane dimethanol dimethacrylate, diethylene glycol diacrylate, diethylene glycol dimethacrylate, dipropylene glycol diacrylate, dipropylene glycol dimethacrylate, ethylene glycol diacrylate, ethylene glycol dimethacrylate, 1,6 hexanediol diacrylate, 1,6 hexanediol dimethacrylate, neopentyl glycol diacrylate, neopentyl glycol dimethacrylate, tetraethylene glycol diacrylate, tetraethylene glycol dimethacrylate, triethylene glycol diacrylate, triethylene glycol dimethacrylate, tripropylene glycol diacrylate, tripropylene glycol dimethacrylate, pentaerythritol triacrylate, trimethylolpropane triacrylate, trimethylolpropane trimethacrylate, dipentaerythritol pentaacrylate, di-trimethylolpropane tetraacrylate, and pentaerythritol tetraacrylate; divinyl esters, such as divinyl adipate; divinyl compounds, such as divinyl sulfide, divinyl sulfone compounds of allyl methacrylate, allyl acrylate, cyclohexanedimethanol divinyl ether diallylphthalate, and diallyl maleate; and dienes such as butadiene, isoprene, and mixtures thereof.

23. The nanolatex particle of claim 1, wherein said W monomer is a water-soluble monomer selected from the group consisting of: 2-phosphatoethyl acrylate potassium salt; 3-phosphatopropyl methacrylate ammonium salt; vinylphosphonic acid, and salts thereof; vinylcarbazole; vinylimidazole; vinylpyrrolidone; vinylpyridines; acrylamide; methacrylamide; maleic acid and salts thereof; sulfopropyl acrylate and methacrylate; acrylic acid and salts thereof; methacrylic acid and salts thereof; N-vinylpyrrolidone; acrylic esters of alkylphosphonates, styrenics, acrylic, and methacrylic monomers containing amine or ammonium functionalities; methacrylic esters of alkylphosphonates, styrenics, acrylic and methacrylic monomers containing amine or ammonium functionalities; styrenesulfonic acid and salts thereof; acrylic and methacrylic esters of alkylsulfonates, vinylsulfonic acid, and salts thereof; vinylpyridines; hydroxyethyl acrylate; glycerol acrylate; methacrylate esters; (meth)acrylamide; and N-vinylpyrrolidone.

24. The nanolatex particle of claim 1, wherein said W monomer is a water-insoluble monomer selected from the group consisting of methyl methacrylate; ethyl methacrylate; isobutyl methacrylate; 2-ethylhexyl methacrylate; benzyl methacrylate; cyclohexyl methacrylate; glycidyl methacrylate; acrylic/acrylate esters such as methyl acrylate, ethyl acrylate, isobutyl acrylate, 2-ethylhexyl acrylate, benzyl methacrylate, phenoxyethyl acrylate, cyclohexyl acrylate, and glycidyl acrylate; styrenics such as styrene, a-methylstyrene, ethylstyrene, 3- and 4-chloromethylstyrene, halogen-substituted styrenes, and alkyl-substituted styrenes; vinyl halides; vinylidene halides; N-alkylated acrylamides; methacrylamides; vinyl esters, such as vinyl acetate and vinyl benzoate; and allyl alcohol and its ethers and esters.

25. The nanolatex particle of claim 1, wherein said Z monomer is a polyethylene glycol macromonomer having a molecular weight of between 500 and 5000.

26. The nanolatex particle of claim 1, wherein said Z monomer is a polyethylene glycol backbone chain with specific functional end groups at each end, which allows said polyethylene glycol to act as a linking group between two materials through said two functional end groups.

27. The nanolatex particle of claim 1, wherein said Z polyethylene glycol macromonomer contains a radical polymerizeable group at one end.

28. The nanolatex particle of claim 27, wherein said radical polymerizeable group is selected from the group consisting of: methacrylate; acrylate; acrylamide; methacrylamide; styrenic; allyl; vinyl; maleimide; and maleate ester.

29. The nanolatex particle of claim 26, wherein said Z polyethylene glycol macromonomer contains a reactive chemical functionality at one end servable as an attachment point for other chemical units.

30. The nanolatex particle of claim 29, wherein said reactive chemical functionality is selected from the group consisting of: alcohols; thiols; carboxylic acids; primary amines; secondary amines; vinylsulfonyls; aldehydes; epoxides; hydrazides; succinimidyl esters; maleimides; a-halo carbonyl moieties; iodoacetyls; isocyanates; isothiocyanates; and aziridines.

31. The nanolatex particle of claim 29, wherein said reactive chemical functionality is servable as an attachment point for linkers designed to form covalent bonds between the reactive chemical functionality on the loaded latex and an attachment group on a bio molecule.

32. The nanolatex particle of claim 31, wherein said attachment group on a bio molecule is selected from the group consisting of: amine; alcohol; carboxylic acid from amino acids; thiol from amino acids; peptides; protein; cells; RNA; and DNA.

33. The nanolatex particle of claim 31, wherein said linkers are selected from the group consisting of: hetero-bifunctional linkers and homo-bifunctional linkers.

34. The nanolatex particle of claim 31, wherein said linkers are selected from the group consisting of: bis-sulfosuccinyl-suberate, 3-[2-(aminoethyl)dithio]propionic acid; p-azidobenzoylhydrazide; bis-maleimidohexane; N-succinimidyl-5-acetylthioacetate; N-Sulfosuccinimidyl-4-azidophenyl-1-3'-dithiopropionatte; Succinimidyl 4-[p-maleimidophenyl] butyrate; N-Succinimidyl[4-iodoacetyl]aminobenzoate; Sulfosuccinimidyl-[perfluoroazidobenzamido]ethyl-1,3'-dithiopropionate; Succinimidyl 3-[bromoacetamido]propionate; Sulfosuccinimidyl 2-[7-amino-4-methylcoumarin-3-acetamido]ethyl-1,3'dithiopropionate; 3-(2-Pyridyldithio) propionyl hydrazide); N-e-Maleimidocaproyloxy] succinimide ester; N-[4-(p-Azidosalicylamido) butyl]-3'-(2'-pyridyldithio)propionamide; Succinimidyl 4-[N-maleimidomethyl]cyclohexane-1-carboxylate; 4-(4-N-Maleimidophenyl)butyric acid hydrazide hydrochloride; Disuccinimidyl suberate; Lomant's Reagent; Sulfosuccinimidyl[2-6-(biotinamido)-2-(p-azidobenzamido)-hexanoamido]-ethyl-1,3'-dithiopropionate; B-[Tris(hydroxymethyl) phosphino]propionic acid (betaine); (Sulfosuccinimidyl 4-[p-maleimidophenyl]butyrate); Bis-Maleimidoethane; Bis-[b-(4-Azidosalicylamido)ethyl]disulfide; Succinimidyl 4-[N-maleimidomethyl]cyclohexane-1-carboxy-[6-amidocaproate]; N-[p-Maleimidophenyl]isocyanate; m-Maleimidobenzoyl-N-hydroxysulfosuccinimide ester; Sulfosuccinimidyl 4-N-maleimidomethyl cyclohexane-1-carboxylate; Bis[sulfosuccinimidyl]suberate; N-[g-Maleimidobutyryloxy]sulfosuccinimide ester; N-succinimidyl 4-pentynoate; and N-succinimidyl 4-azidoylbutanoate.

35. The nanolatex particle of claim 1, wherein said particle has a volume-average hydrodynamic diameter of less than 100 nm.

36. The nanolatex particle of claim 1, wherein said particle has a volume-average hydrodynamic diameter of from 8 to 50 nm.

37. The nanolatex particle of claim 1, wherein said fluorescent dye compound is present in an amount of from 0.01 to 5 percent by weight.

38. The nanolatex particle of claim 1, wherein said fluorescent dye emits in the range of from 600 to 900 nm.

39. The nanolatex particle of claim 1, wherein Y is divinyl benzene.

40. The nanolatex particle of claim 39, wherein W is ethylstyrene.

41. The nanolatex particle of claim 40, wherein X is methoxyethyl methacrylate.

42. The nanolatex particle of claim 41, wherein Z is poly (ethylene glycol) monomethyl ether methacrylate.

43. The nanolatex particle of claim 42, wherein the water dispersible, near-infrared tricarbocyanine, enamine-functionalized dye compound having a Stokes shift of greater than 50 nm is represented by the following formula:

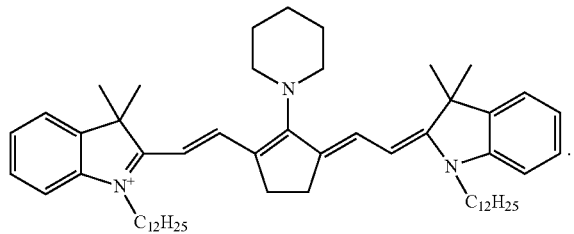

44. The nanolatex particle of claim 42, wherein the water dispersible, near-infrared tricarbocyanine, enamine-functionalized dye compound having a Stokes shift of greater than 50 nm is represented by the following formula:

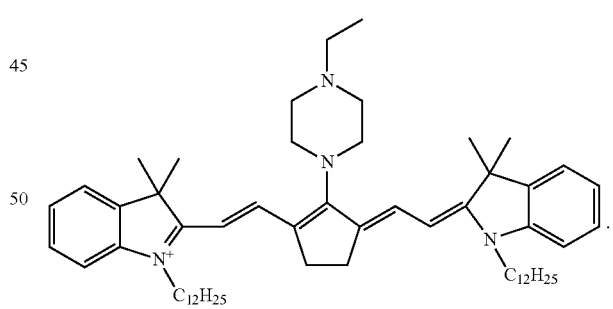

* * * * *